US011690640B2

(12) United States Patent
Ryan, Jr. et al.

(10) Patent No.: US 11,690,640 B2
(45) Date of Patent: Jul. 4, 2023

(54) SYSTEMS AND METHODS FOR SURGICAL PROCEDURES USING TORQUE DRIVEN GUIDE WIRE

(71) Applicant: Interscope, Inc., Northbridge, MA (US)

(72) Inventors: Jeffery B. Ryan, Jr., Whitinsville, MA (US); Sean Buxton, Northbridge, MA (US); Corey Libby, Northbridge, MA (US); Anthony DiBella, Northbridge, MA (US); Nathan Casey, Northbridge, MA (US)

(73) Assignee: INTERSCOPE, INC., Northbridge, MA (US)

( * ) Notice: Subject to any disclaimer, the term of this patent is extended or adjusted under 35 U.S.C. 154(b) by 304 days.

(21) Appl. No.: 17/184,080

(22) Filed: Feb. 24, 2021

(65) Prior Publication Data

US 2021/0267620 A1 Sep. 2, 2021

Related U.S. Application Data

(60) Provisional application No. 62/981,302, filed on Feb. 25, 2020.

(51) Int. Cl.
*A61B 17/32* (2006.01)
*A61B 90/00* (2016.01)

(52) U.S. Cl.
CPC ........ *A61B 17/32002* (2013.01); *A61B 90/39* (2016.02); *A61B 2017/320052* (2013.01);
(Continued)

(58) Field of Classification Search
CPC .............. A61B 17/22; A61B 17/32002; A61B 17/320758; A61B 90/39;
(Continued)

(56) References Cited

U.S. PATENT DOCUMENTS 5,314,438 A * 5/1994 Shturman ............. A61M 25/01
606/159
5,318,576 A 6/1994 Plassche et al.
(Continued)

FOREIGN PATENT DOCUMENTS

WO WO-2019/070874 A1 4/2019

OTHER PUBLICATIONS

International Search Report and Written Opinion for PCT Appl. Ser. No. PCT/US/2021/019417 dated Jun. 16, 2021 (15 pages).

*Primary Examiner* — Ryan J. Severson
(74) *Attorney, Agent, or Firm* — Foley & Lardner LLP

(57) ABSTRACT

Systems and methods for removing a material from a lumen or duct include a guide wire to navigate to the material and a cutting assembly that can then be guided along the guide wire to reach the material. A proximal wire end can be connected to a pump device configured to provide an irrigation substance along a delivery channel of the guide wire and release the irrigation substance at a distal wire end. A power source can apply a current to the guide wire to magnetize a coupling assembly disposed on the guide wire. The cutting assembly can couple to the guide wire by engaging a locking mechanism of the cutting assembly with a coupling assembly of the guide wire. The locking mechanism can receive torque provided by a motor coupled to the proximal wire end of the guide wire to rotate the cutting tool of the cutting assembly to remove the material.

20 Claims, 10 Drawing Sheets

(52) U.S. Cl.
CPC . *A61B 2090/3966* (2016.02); *A61B 2217/005* (2013.01); *A61B 2217/007* (2013.01)

(58) Field of Classification Search
CPC ........... A61B 2017/22038; A61B 2017/22049; A61B 2017/22081; A61B 2017/320052; A61B 2090/3966; A61B 2217/005; A61B 2217/007
See application file for complete search history.

(56) References Cited

U.S. PATENT DOCUMENTS

| | | | |
|---|---|---|---|
| 5,360,432 | A | 11/1994 | Shturman |
| 9,204,868 | B2 | 12/2015 | Furlong et al. |
| 10,265,087 | B2 * | 4/2019 | Furlong .................. A61B 1/005 |
| 10,765,446 | B2 * | 9/2020 | Higgins ......... A61B 17/320758 |
| 11,564,670 | B2 * | 1/2023 | Furlong ............. A61B 10/0275 |
| 2015/0032024 | A1 * | 1/2015 | Furlong ............. A61B 1/00133 600/566 |
| 2016/0081705 | A1 * | 3/2016 | Furlong ............. A61B 1/00094 606/114 |
| 2018/0235653 | A1 | 8/2018 | Higgins et al. |
| 2019/0380724 | A1 * | 12/2019 | Furlong ............... A61B 17/221 |
| 2020/0281619 | A1 * | 9/2020 | Ryan, Jr. ............ A61B 18/1485 |
| 2021/0267620 | A1 * | 9/2021 | Ryan, Jr. ................ A61B 90/39 |

* cited by examiner

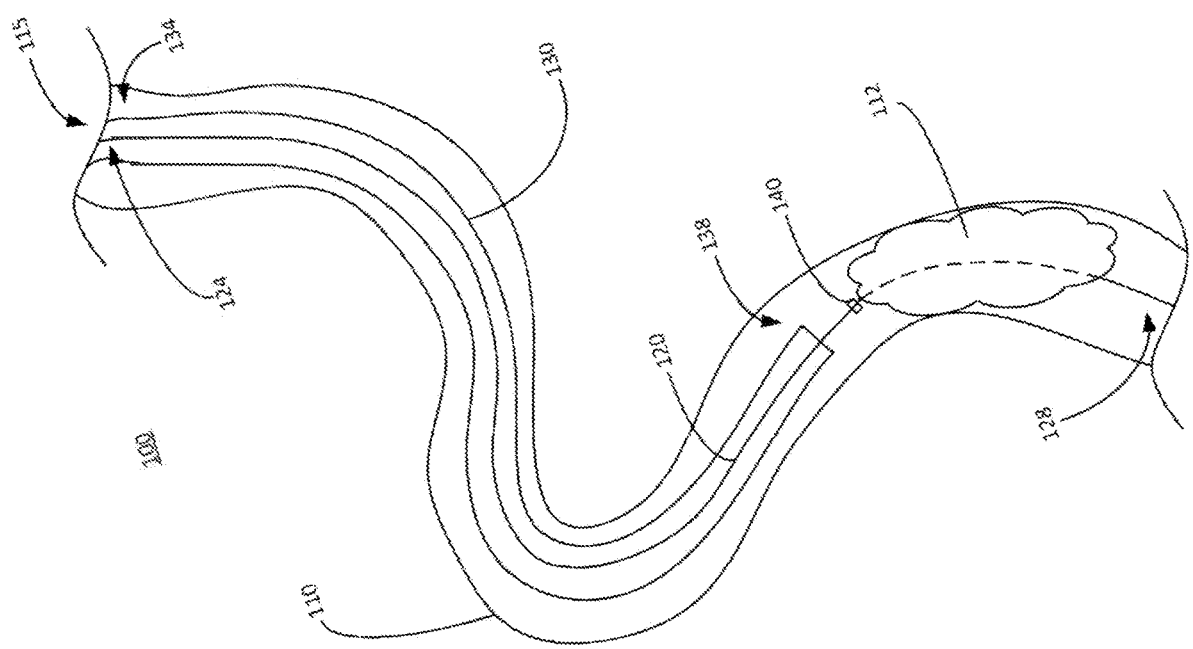

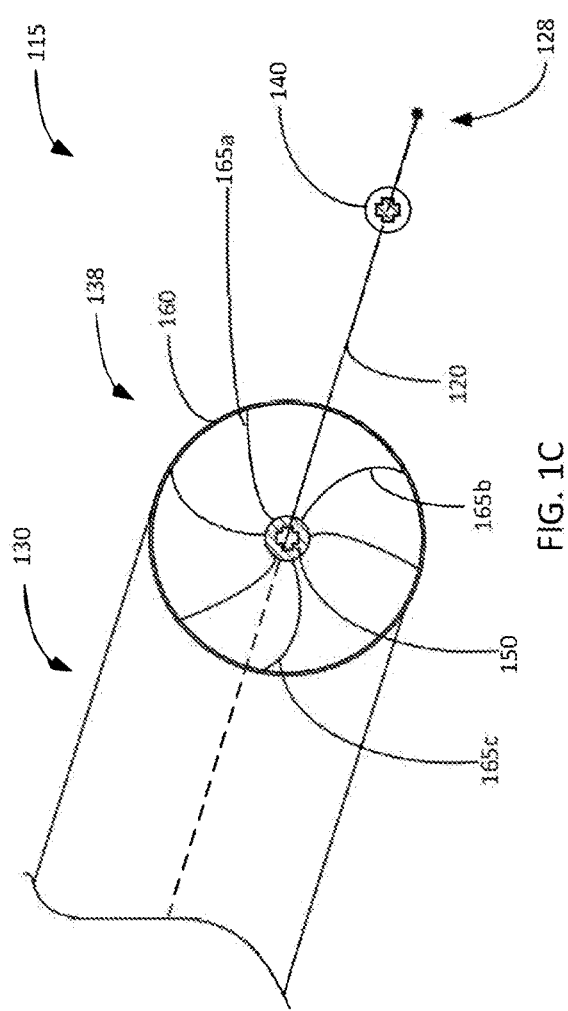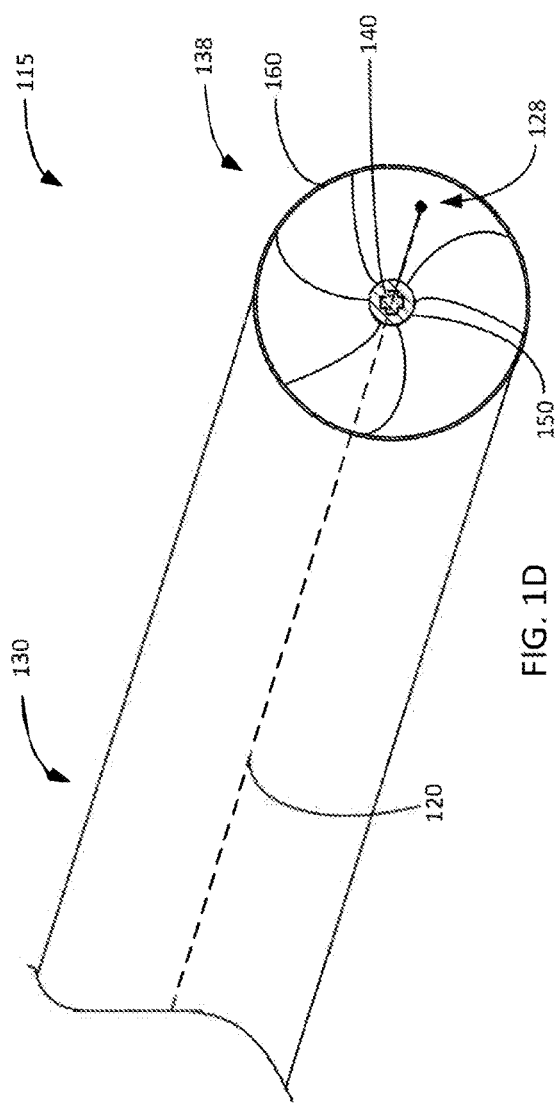

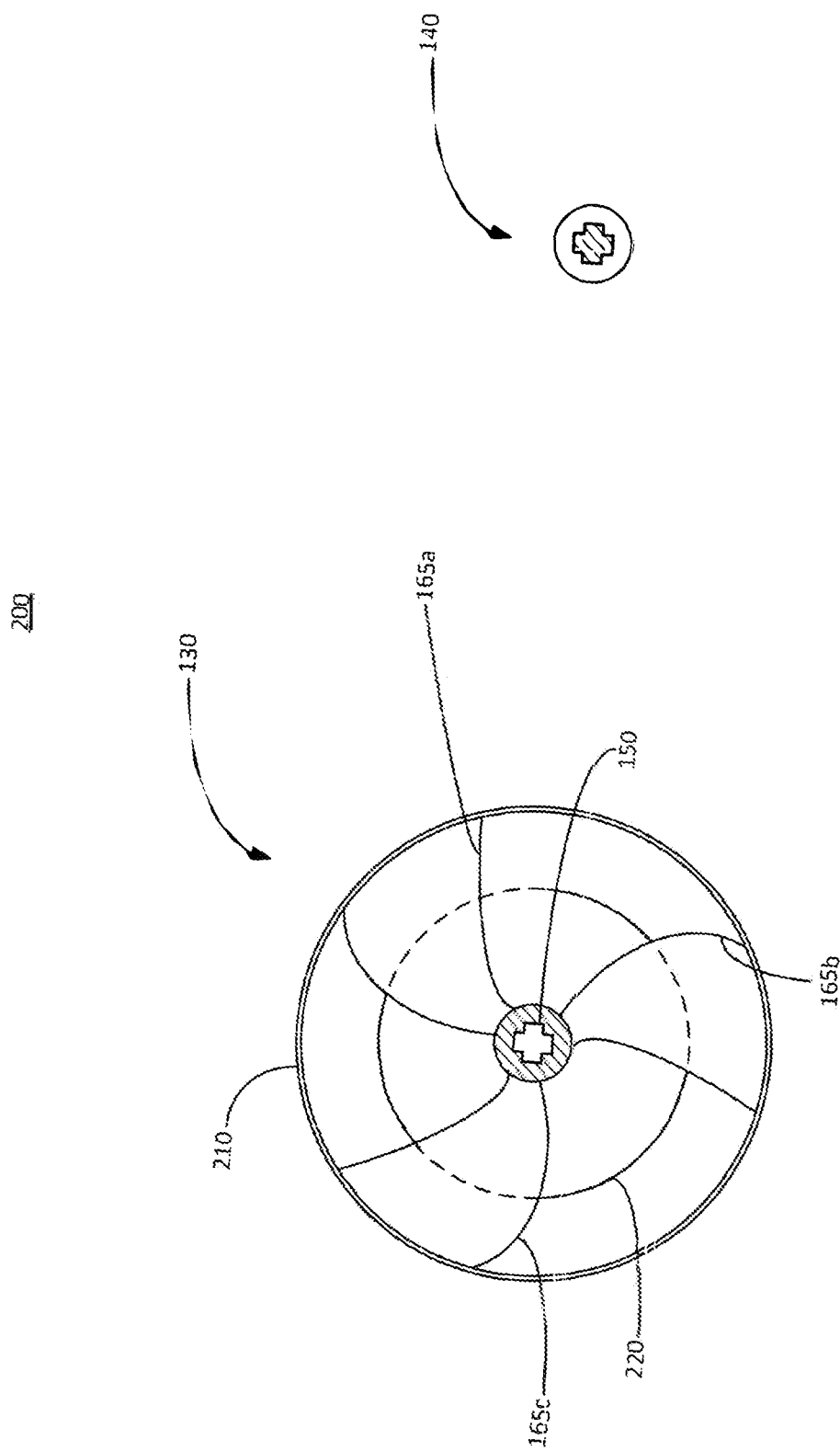

SYSTEMS AND METHODS FOR SURGICAL PROCEDURES USING TORQUE DRIVEN GUIDE WIRE

CROSS-REFERENCE TO RELATED APPLICATIONS

The present application claims the benefit of and priority to U.S. Provisional Application No. 62/981,302, filed Feb. 25, 2020, titled "SYSTEMS AND METHODS FOR ENDOSCOPIC PROCEDURES USING TORQUE DRIVEN GUIDE WIRE," the entire disclosure of each of which is incorporated by reference herein for any and all purposes.

BACKGROUND

A surgical tool can be inserted into an organ or a cavity of a body for examination. A doctor or surgeon can examine or observe the organ or the cavity via a camera of the surgical tool. The surgical tool can dissect or cut tissue in the organ or the cavity, and remove the tissue from the body.

SUMMARY

At least one aspect relates to a system for removing a material from a lumen or duct. The system can include a guide wire extending from a proximal wire end to a distal wire end. The system can include a cutting assembly. The cutting assembly can include a flexible tube extending from a proximal tube end to a distal tube end. The cutting assembly can include a cutting tool coupled to the distal tube end, the cutting tool configured to remove the material. The cutting assembly can include a locking mechanism configured to couple with the guide wire to receive torque provided by a motor coupled to the proximal wire end to rotate the cutting tool to remove the material.

At least one aspect relates to a method for removing a material from a lumen or duct. The method can include inserting a guide wire into an endoscope-working channel into the lumen or duct, the guide wire extending from a proximal wire end to a distal wire end. The method can include moving a cutting assembly to the material using the guide wire, the cutting assembly comprising a flexible tube extending from a proximal tube end to a distal tube end, a cutting tool coupled to the distal tube end, and a locking mechanism. The method can include coupling the locking mechanism of the cutting assembly with the coupling assembly of the guide wire. The method can include removing, by the cutting tool in response to the guide wire receiving torque provided by a motor coupled to the proximal wire end, the material from the lumen or duct. The method can include retrieving, through the cutting assembly, the material removed from the lumen or duct.

These and other aspects and embodiments are discussed in detail below. The foregoing information and the following detailed description include illustrative examples of various aspects and embodiments, and provide an overview or framework for understanding the nature and character of the claimed aspects and embodiments. The drawings provide illustration and a further understanding of the various aspects and embodiments, and incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every drawing labels every component. In the drawings:

FIG. 1A is a schematic diagram of the material removal system in the lumen or duct according to embodiments of the present disclosure.

FIG. 1C shows a perspective view of the according to embodiments of the present disclosure.

FIG. 1D shows a perspective view of locking mechanism of the cutting assembly coupled to the coupling assembly according to embodiments of the present disclosure.

FIG. 2C shows a front view of the cutting assembly according to embodiments of the present disclosure.

FIG. 2D shows a front view of the coupling assembly according to embodiments of the present disclosure.

DETAILED DESCRIPTION

Figure 1B:
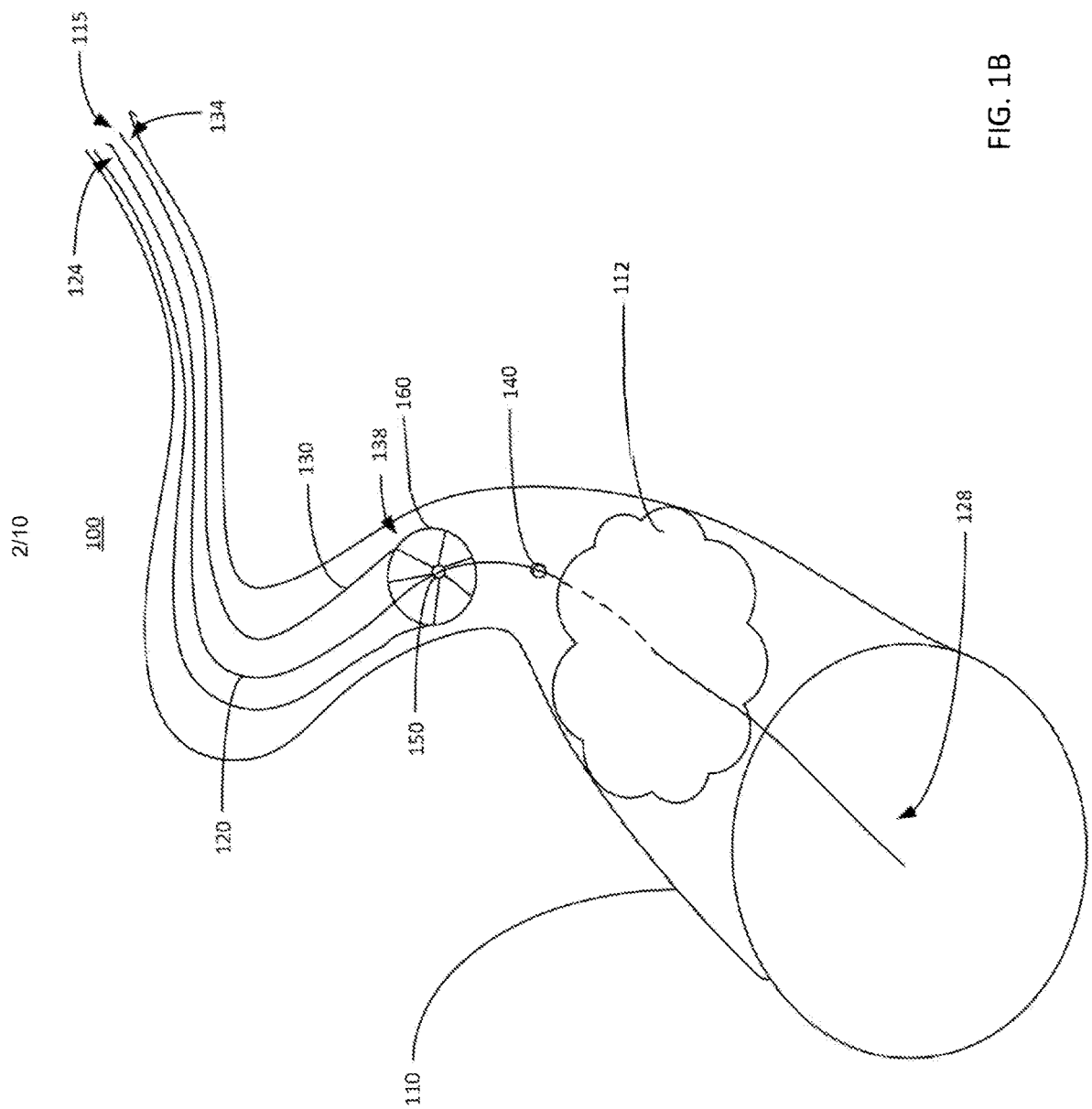
FIG. 1B is a perspective view of the material removal system in the lumen or duct according to embodiments of the present disclosure.

The present disclosure will be more completely understood through the following description, which should be read in conjunction with the drawings. In this description, like numbers refer to similar elements within various embodiments of the present disclosure. Within this description, the claims are explained with respect to embodiments. The skilled artisan will readily appreciate that the methods, apparatus and systems described herein are merely exemplary and that variations can be made without departing from the spirit and scope of the disclosure.

A. Surgical Solutions Overview

Technologies provided herein are directed towards an improved material removal system that can efficiently and precisely extract or remove stenosis, scarring, or a mass from a lumen or duct. The improved material removal system can maneuver through a flexible endoscope or as part of a percutaneous procedure and fluoroscopically maneuvered into a cavity or organ of the patient to cut or dissect stenosis, scarring, or masses. The improved material removal system can retrieve debrided samples of the tissue without having to use another suction device or a drilling device.

The material removal system can be used in various applications. In additional embodiments, the material removal system can be described in detail in section B of the following description. It should, however, be appreciated that the scope of the present disclosure is not limited to a single type of material removal system, such as for use with gastrointestinal ("GI") scopes or percutaneous procedures, but extends to any type of flexible cutting assembly, including but not limited to bronchoscopes, gastroscopes, laryngoscopes, or other medical devices that can be used to treat patients. The material removal system can treat various parts or portions of the body, such as the ear, esophagus, stomach, small intestine, large intestine, pancreatic ducts, or other hollow lumens.

B. Material Removal Systems and Methods

A material removal system and methods thereof in accordance with the present disclosure can include components such as a guide wire, a cutting assembly, and at least one external device. The at least one external device can include, for example, a motor, a pump device, or a display device. A hand piece can couple to the components, and an operator can use the hand piece to control the components. The operator can insert the guide wire into a cavity as part of an endoscopic procedure or as part of a percutaneous procedure that involves accessing organs or other tissue via a needle-puncture of the skin. The operator can navigate the guide wire in lumens or ducts to reach the material. The operator can manually push the guide wire or the motor can rotate the guide wire to maneuver the wire. The operator can navigate the guide wire using fluoroscopic or endoscopic ultrasound imaging modalities. The operator can also navigate the guide wire using stereotactic robotic assisted navigation.

After the guide wire is near the material, the operator can guide the cutting assembly along the guide wire to the material. The operator can maneuver the cutting assembly along the guide wire until a locking mechanism of the cutting assembly is positioned to couple to a coupling assembly of the guide wire. By coupling the locking mechanism to the coupling assembly, the operator or the motor can rotate the guide wire, which will cause the guide wire to rotate the locking mechanism, which will cause a cutting tool coupled to the locking mechanism to cut the material in the lumen or duct. The operator can also disengage the locking mechanism from the coupling mechanism to maneuver the cutting assembly along the guide wire. The cutting assembly can also include an expulsion mechanism (e.g. flushing, washing, transmission, or other features to provide irrigation substance into the lumen or duct and to the material) using, for example, a pump device. Once the cutting tool cuts the material, the operator can retrieve the material. The cutting assembly can connect to a pump device to retrieve the material. The pump device can coupled to or be part of the hand piece, which the operator can use to suction the material from the lumen or duct.

Referring to FIG. 1A, depicted is a schematic 100 diagram of a lumen or duct 110 and a material removal system 115. The lumen or duct 110 can include the material 112 situated within a portion of the lumen or duct 110. The material removal system 115 can include a guide wire 120 and a cutting assembly 130. The guide wire 120 can include a coupling assembly 140. The cutting assembly 130 can include a locking mechanism 150 and a cutting tool 160. The cutting tool 160 can include one or more blades 165.

For example, referring further to FIG. 1A, for performing a procedure to remove material 112 from the bile duct, the guide wire 120 can be introduced into the bile duct (e.g., using EUS). The cutting assembly 130 can move along the guide wire 120 to the target site at which the material 112 is located. The coupling assembly 140 of the guide wire 120 can couple to the locking mechanism 150 of the cutting tool 160, and the locking mechanism 150 can drive the cutting tool 160 to remove the material 112.

The lumen or duct 110 can be from one of various types, such as an artery, an arteriole, a capillary, a venule, or a vein. The lumen or duct 110 can also be a tube, canal, or socket such as an ear canal, a nose canal, bile duct, intestine, esophagus, or stomach. The schematic 100 can illustrate a portion of the lumen or duct 110. The lumen or duct 110 can include a length of, for example, 600 micrometers, 5 centimeters, 10 inches, 100 inches, 10 meters, 20 meters, etc. The lumen or duct 110 can include a cross-sectional area of, for example, 1 sq mm to 500 sq mm, or in some embodiments, 2.5 square centimeters, 10 square centimeters, 20 square centimeters, 30 square centimeters, etc. In some embodiments, the schematic 100 can replace or interchange the lumen or duct 110 with other portions of a human body accessible through a bodily cavity or by a surgical procedure, such as hollow organs, tubes, canals, pathways, or other sockets. The cavity can include, for example, an archenteron, sinus, lumen, duct, or other natural hollow or sinus. In some embodiments, a dissection, such as of an arm or stomach, creates the cavity to access the material 112 within the lumen or duct 110. In some embodiments, the lumen or duct 110 can include the material 112.

The material 112 can be referred to as, and use interchangeably with other descriptive terms, such as object, tissue, or content within the lumen or duct 110. The material 112 can manifest overtime within the lumen or duct 110 to narrow or block the path or the opening of the lumen or duct. For example, the materials 112 form due to damage or an injury to the lumen or duct 110, such as a chronic infection. The material 112 can be a liquid, a solid, or a combination of a liquid and a solid item that the operator can remove, extract, examine, or collect from the lumen or duct 110. The walls of the lumen or duct 110 can receive an indication of the damaged lumen or duct 110. The stenosis or mass can fill in or plug the damaged portion of the lumen or duct 110. The clogging or the blockage of the lumen or duct 110 can refer to the material 112.

In some embodiments, a size of the material 112 (e.g. length, width, or height) can be determined using a distance sensor. The distance sensor can measure the distance traversed by the guide wire 120 through the material 112. In some embodiments, the distance sensor can measure the distance traversed by the guide wire 120 through the lumen or duct 110. In some embodiments, the material removal system 115 can determine a size of the material 112 based on the distance. For example, the distance sensor can measure a distance the guide wire 120 traversed through the material 112. The distance sensor can initiate measurement based on an indication of a contact or pressure representing the material 112. The guide wire 120 can traverse through the material 112. Once the guide wire 120 passes the material, the distance sensor does not receive the indication of the contact or pressure representing the material 112, indicating an end of the material 112. The distance sensor can determine the size of the material 112 based on the distance measured between the contact with the material 112 and the absent of the material 112. In some embodiments, the distance sensor can perform a calculation, such as a subtraction between the initiation point and the termination point of the distance measurement to determine the size of the material 112. In some embodiments, the guide wire 120 can include a camera or a scope to determine the size of the material 112.

The guide wire 120 can navigate in the lumen or duct 110. The guide wire 120 maneuvers into the lumen or duct 110. The guide wire 120 can navigate in the lumen or duct 110 to reach the material 112. The guide wire 120 can be composed of at least one of metal, steel, plastic, titanium, nickel, carbon fiber, or other alloys. The guide wire 120 can include a coding comprising at least one chemical compound for insertion into the lumen or duct 110, such as polymer, hydrophilic, nitinol, fluoropolymer, or a combination of two or more compounds to increase durability, lubrication, flexibility, or corrosion resistance of the guide wire 120. The chemical compound can cause the guide wire 120 to emit light while being navigated. The guide wire 120 can be radio opaque to x-rays or similar radiation. The emitted light allows the operator to maneuver the guide wire 120 using fluoroscopic imaging techniques. The guide wire 120 can include one or more textures or grooves, such as a spiral, a twist, frets, or other protrusion or engraving.

The guide wire 120 can include a proximal wire end 124 and a distal wire end 128. The guide wire 120 can include the coupling assembly 140 disposed at the distal wire end 128. The guide wire 120 can be inserted into the lumen or duct 110 with the distal wire end 128. The guide wire 120 can navigate along the path of the lumen or duct 110 to reach at least one material 112 (i.e. object, tissue, etc.) within lumen or duct 110. The material 112 within the lumen or duct 110 can be a lesion. The guide wire 120 can navigate past the treatment site. The guide wire 120 can be in contact with the material 112. In some embodiments, the guide wire 120 can be configured to navigate 1, 2, 3, 4, 5, 6, 7, 8, 9, or 10 mm into the material 112. In some embodiments, the guide wire 120 can be configured to navigate 1, 2, 3, 4, 5, 6, 7, 8, 9, or 10 cm past the material 112.

The guide wire 120 can include or be coupled to one or more sensors, such as a proximity sensor, an electromagnetic sensor, an optical stereotactic sensor, a camera, a light sensor, a light source, a pressure sensor, a radar sensor, a flow sensor, a flex sensor, an impact sensor, a distance sensor, or other sensor for examination of the lumen or duct 110. The one or more sensors can be located, for example, on the distal wire end 128 of or inside the guide wire 120. The sensors can provide data for navigating the guide wire 120 through the lumen or duct 110. In some embodiments, the material removal system 115 can use the one or more sensors to determine a location of the material 112. In some embodiments, the material removal system 115 can use the one or more sensors to inspect or investigate the material 112 within the lumen or duct 110. For example, the guide wire 120 can be maneuvered through the lumen or duct 110 using a driving device (not shown) or manually by an operator. The light source can include a light emitting diode ("LED"), incandescent lamps, compact fluorescent, halogen, neon, or other types of lighting elements. The light source can emit light and the camera can initiate recording. The camera can receive various images of the lumen or duct wall 110 and transmit the images to a display device (not shown) for display to the operator. The display device can generate or display the images based on the received visual information for the operator to view inside the lumen or duct 110. The camera of the guide wire 120 can visualize the material 112 and provide an indication of the material 112. The guide wire 120 can be maneuvered to traverse the material 112 based on the camera of the guide wire 120 not receiving an indication of the material 112. In some embodiments, the guide wire 120 or the one or more sensors can receive an indication of a second material 112.

The sensors can determine the presence of the lumen or duct 110. The sensors can determine or detect the presence of the material 112 to be removed. The material removal system 112 can use the sensors to identify the material 112 based on contact with the material 112. For example, the guide wire 120 can include a pressure sensor. The pressure sensor can receive an indication of a contact, a push, a density, or other pressure information that indicates the material 112. The guide wire 120 can be maneuvered into the lumen or duct 110 and navigate within the lumen or duct 110, similar to the previous example. The guide wire 120 can receive, using the pressure sensor, an indication of a pressure with the material 112. The guide wire 120 can traverse through the material 112 while receiving the indication of the pressure. The guide wire 120 can pass the material 112 based on not receiving an indication of the pressure.

The guide wire 120 can be a flexible wire for medical insertion into the lumen or duct 110. The guide wire 120 can be flexible as to not introduce injuries, tears, wounds, or other damages to the lumen or duct 110 or to the guide wire 120. The flexibility of the guide wire 120 can facilitate the navigation of the guide wire 120 within the lumen or duct wall 110. For example, the lumen or duct 110 can include curves, bumps, or otherwise non-linear paths. The material 112 can be located past the non-linear path within the lumen or duct 110. The guide wire 120 can push, bump, or impact the lumen or duct wall 110 to turn through the non-linear path of the lumen or duct 110. The flexible guide wire 120 can reduce the chance of damaging the lumen or duct wall 110 while navigating to the material 112.

The guide wire 120 can be a flexible coil, a navigation wire, a motorized wire, or a braid. The guide wire 120 can have a shape, such as a cylinder, a cone, or other prisms. The guide wire 120 can be composed of at least one of metal, steel, nickel, titanium, nitinol, or other metallic alloy. The guide wire 120 can have a length. The length can be 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 cm. The length of the guide wire 120 can be greater than the length of the cutting assembly 130. For example, the length of the guide wire 120 can be 50 cm meters and the length of the cutting assembly 130 can be 75 cm. The guide wire 120 can include a diameter sized for inserting the guide wire 120 into the lumen or duct 110. The diameter can be 100, 200, 300, 400, 500, 600, 700, 800, 900, or 1000 nanometers. The diameter of the guide wire 120 can enable insertion of the guide wire 120 into the cutting assembly 130 to provide a course or navigation path towards the material 112 within the lumen or duct 110.

The flexibility of the guide wire 120 allows it to maintain performance even in sections of the guide wire 120 that are bent. For example, the lumen or duct wall 110 can have a bend of 120 degrees. The cutting assembly 130, including the components within the cutting assembly 130, such as the guide wire 120, can be bent 120 degrees. The bent guide wire 120 can maintain the rotational performance at the 120 degrees bent. In some embodiments, a sheath or lining surrounds the guide wire 120 to avoid frictional contact between the outer surface of the guide wire 120 and other surfaces. In some embodiments, Polytetrafluoroethylene ("PFTE") coats the guide wire 120 to reduce frictional contact between the outer surface of the guide wire 120 and other surfaces, such as the inner wall of the lumen or duct 110. In some embodiments, the guide wire 120 has an outer diameter that is smaller than the diameter of the instrument channel in which the cutting assembly 130 navigates. For example, in some embodiments, the outer diameter of the guide wire 120 can be within the range of 1-4 millimeters. In some embodiments, the length of the guide wire 120 exceeds the length of the cutting assembly 130.

The distal wire end 128 of the guide wire 120 can include at least one sensor to navigate the guide wire 120 into the lumen or duct 110. The distal wire end 128 can also include at least one sensor to locate the material 112. In some embodiments, the operator navigates the distal wire end 128 past the material 112. The operator can then providing the cutting assembly 130 to debride the material 112. The sensor can be located at the distal wire end 128 of the guide wire 120. The guide wire 120 can include a groove or a pattern, such as a spiral, a twist, or a bump to facilitate movement of the cutting assembly 130. In some embodiments, guide wire 120 can also include a lining that fits around the guide wire 120 for the cutting assembly 130 to maneuver on while traversing the guide wire 120. In some embodiments, the lining can prevent air or other fluids to seep between the cutting assembly 130 and the guide wire 120.

In some embodiments, the guide wire 120 can be an extendable or a retractable wire. The guide wire 120 can extend or retract via a manual operation or by an electrically operated device. The guide wire 120 can be configured to couple to the cutting assembly 130, such as to the locking mechanism 150 of the cutting assembly 130. For example, the proximal wire end 124 of the guide wire 120 can be configured to couple adjacent to the distal tube end 138 of the cutting assembly 130. In some embodiments, the guide wire 120 can extend in length to increase the distance between the proximal wire end 124 and the distal wire end 128. In some embodiments, the guide wire 120 can retract to decrease a distance between the proximal wire end 124 and the distal wire end 128. For example, the guide wire 120 can extend to maneuver the distal wire end 128 through the material 112. The cutting assembly 130 can maneuver towards the distal wire end 128 of the guide wire 120. The guide wire 120 retracts, as the cutting assembly 130 maneuvers towards the distal wire end 128, for example, to stop the distal wire end 128 from moving based on the movement of the cutting assembly 130.

The cutting assembly 130 can traverse from the proximal wire end 124 to enter the lumen or duct 110 and traverse to the distal wire end 128 to reach the material 112. In some embodiments, the cutting assembly 130 can also include a lining that fits around the guide wire 120 for the cutting assembly 130 to maneuver within the lumen or duct 110 by traversing the guide wire 120. In some embodiments, the lining can prevent air or other fluids to seep between the cutting assembly 130 and the guide wire 120.

The cutting assembly 130 can have a similar composition as the guide wire 120. For example, the cutting assembly 130 can include metal, steel, plastic, titanium, nickel, carbon fiber, or other alloys. The cutting assembly 130 can be composed differently than the guide wire 120. For example, the guide wire 120 can be composed of steel and the cutting assembly 130 can be composed of metal and plastic. The cutting assembly 130 can be composed with higher or lower density, higher or lower malleability, higher or lower flexibility, or other features for ease of traversing the lumen or duct 110. The cutting assembly 130 can be a braided sheath.

The cutting assembly 130 can include a distal tube end 138 and a proximal tube end 134. The proximal tube end 134 can refer to the base, the beginning, or the foundation of the cutting assembly 130. The distal tube end 138 can refer to the tip or the front of the cutting assembly 130. In some embodiments, the cutting assembly 130 can include the guide wire 120 fixed to the distal tube end 138 of the cutting assembly 130. In some embodiments, the distal wire end 128 extends out of the proximal tube end 134 of the cutting assembly 130. In some embodiments, the distal wire end 128 extends out of the distal tube end 138 of the cutting assembly 130 through the locking mechanism 150. The guide wire 120 can be extendable or retractable to increase or decrease a length of the guide wire 120. For example, the guide wire 120 couples to the distal tube end 138 of the cutting assembly 130. In some embodiments, the guide wire 120 extends to increase the length of the guide wire 120 between the distal tube end 138 and the distal wire end 128 of the guide wire 120. In some embodiments, the cutting assembly 130 can maneuver towards the material 112 while retracting the guide wire 120. For example, the guide wire 120 retracts as the cutting assembly 130 maneuvers towards the distal wire end 128.

The cutting assembly 130 can include or be coupled to one or more sensors located at the distal tube end 138, such as a light sensor, electromagnetic sensor, an optical stereotactic sensor, a pressure sensor, an impact sensor, a flow sensor, a radar sensor, a position sensor, or a distance sensor. In some embodiments, the one or more sensors can be located in a different part or portion of the cutting assembly 130, such as the proximal tube end 134 or in between the proximal tube end 134 and the distal tube end 138. In some embodiments, the cutting assembly 130 detects a presence of the lumen or duct 110, or the materials 112. The cutting assembly 130 can be equipped with at least one sensor that can communicate with at least one external device, such as a sensor processing component (not shown) outside the cutting assembly 130 to determine the thickness of material 112 relative the rest of the lumen or duct 110 indicated by the sensor. The sensor can include, for example, a temperature sensor, a pressure sensor, a resistance sensor, an impact sensor, an ultrasonic sensor, or other sensor for medical examination. In some embodiments, the type of material 112 is associated with at least an impedance or a density of the tissue. The sensor can gather temperature information and other sensed information, and provide signals corresponding to such information to the sensor-processing unit. The sensor-processing unit can subsequently identify the type of material 112. In some embodiments, the sensor can be an electrical sensor.

The cutting assembly 130 can couple to the guide wire 120 prior to insertion of the cutting assembly 130 into the lumen or duct 110. The cutting assembly 130 can be maneuvered through the cavity and into the lumen or duct 110 from the proximal tube end 134 to the distal tube end 138. The cutting assembly 130 can traverse the lumen or duct 110 using the guide wire 120. The cutting assembly 130 can receive an indication of the material 112 within the lumen or duct 110 using a pressure sensor, similar to the example of the guide wire 120 previously described. An operator can use the cutting assembly 130 to perform a procedure on the material 112 (or in the lumen or duct 110), such as an extraction, an investigation, or a collection of the material 112 using, for example, an external device connected to the proximal tube end 134.

The cutting assembly 130 can be maneuvered into the lumen or duct 110. The insertion of the cutting assembly 130 can be through the opening or the cavity similar to the guide wire 120. The cutting assembly 130 can be a flexible cutting assembly 130, such that the cutting assembly 130 can turn, bend, or otherwise navigate through curvature of the lumen or duct 110. The cutting assembly 130 can be flexible as to not introduce injuries, tears, wounds, or other damages within the lumen or duct 110 or to the cutting assembly 130, similar to the guide wire 120. For example, the cutting assembly 130 maneuvers into the lumen or duct 110 including a curved portion. The cutting assembly 130 can be navigated through the lumen or duct 110 via the guide wire 120. The guide wire 120 can be in contact with the lumen or duct wall 110, such that the cutting assembly 130 can reach the lumen or duct wall 110 to navigate through the curved portion of the lumen or duct 110. The cutting assembly 130 can reach the curved portion of the lumen or duct 110. The cutting assembly 130 can initiate a bend or a turn in response to reaching or being in contact with the lumen or duct wall 110, such that the cutting assembly 130 curves through the curved portion of the lumen or duct 110 while navigating through the lumen or duct 110 along the guide wire 120.

In some embodiments, the cutting assembly 130 can be inserted into an instrument channel or working channel of an endoscope or any other medical device with an instrument channel. The instrument channel can define a hollow portion or entrance enclosed by an attachment sheath configured for the cutting assembly 130. The attachment can increase the diameter of the cutting assembly 130, provide an additional shape, texture, groove, or other features to the cutting assembly 130, or provide a cover for traversing within the lumen or duct 110.

The cutting assembly 130 can maneuver along the guide wire 120, such as to the proximal wire end 124 of the guide wire 120. The cutting assembly 130 can be inserted into the lumen or duct 110, traverse the lumen or duct 110, be in contact with the lumen or duct wall 110, reach the material 112 within the lumen or duct 110, or otherwise traverse within the lumen or duct 110 using the guide wire 120. The cutting assembly 130 can traverse from the proximal wire end 124 to the distal wire end 128 of the guide wire 120.

The coupling assembly 140 of the guide wire 120 can couple with the locking mechanism 150 of the cutting assembly 130. In some embodiments, the coupling assembly 140 can include at least one groove, at least one hole, or at least one socket to fit with or couple to at least one protruding portion of the locking mechanism 150. In some embodiments, the coupling assembly 140 can include at least one protruding portion to fit with or couple to at least one groove, socket, or hold of the locking mechanism 150 of the cutting assembly 130. The coupling assembly 140 can include both a protruding portion and a socket to couple with the locking mechanism 150. The protruding portion and the socket can include pin interconnects, magnets, friction fitting grooves, or other attachment features.

The coupling assembly 140 can couple, link, or connect to the locking mechanism 150 of the cutting assembly 130. For example, the cutting assembly 130 can move along the guide wire 120 to reach the coupling assembly 140 within the lumen or duct 110. The guide wire 120 can rotate, which rotates the coupling assembly 140, which will also rotate when coupled to the locking mechanism 150. The rotation of the guide wire 120 can include, for example, the rotation of the proximal wire end 124 or the rotation of the distal wire end 128. The rotation of the coupling assembly 140 can be in response to the rotation of the rotation of the distal wire end 128 or the rotation of the proximal wire end 124.

The coupling assembly 140 can be located at the distal wire end 128. The coupling assembly 140 can be located a distance from the distal wire end 128. The coupling assembly 140 can be a distance from the distal wire end 128 to accommodate for the size and the length of the material 112 in the lumen or duct 110. The distance can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 cm. In some embodiments, the coupling assembly 140 relocates to different portion of the guide wire 120. For example, the coupling assembly 140 couples 1 centimeter from the distal wire end 128 of the guide wire 120. The material 112 within the lumen or duct 110 can have a length. The length can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm. The guide wire 120 can traverse a first side of the material 112 to reach a second side of the material 112. For example, the material 112 can push the coupling assembly 140 from 1 centimeter from the distal wire end 128 to 10 centimeters from the distal wire end 128.

The coupling assembly 140 can be composed of materials similar to, for example, the guide wire 120, the cutting assembly 130, the cutting tool 160, or the locking mechanism 150. The coupling assembly 140 is at a portion of the guide wire 120 including, for example, at the distal wire end 128 or a distance from the distal wire end 128. The distance from the distal wire end 128 can include, for example, at least 1 millimeter, 5 centimeters, 10 centimeters, or 2 inches from the distal wire end 128. The coupling assembly 140 can be in contact with the material 112 within the lumen or duct 110. The coupling assembly 140 can be a distance from the material 112. The distance can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm. The coupling assembly 140 can have a similar size to the locking mechanism 150. For example, the coupling assembly 140 and the locking mechanism 150 can both have a diameter of 0.5, 1, 2, 3, 4, 5, 6, 7, 8, 9, or 10 mm. The coupling assembly 140 can include a hollow portion or a protruding portion, opposite to the locking mechanism 150. The hollow portion of the protruding portion can include similar shape to the locking mechanism 150, such as a cross, a square, a triangle, or other geometry. For example, if the locking mechanism 150 include a cross hollow portion, the coupling assembly 140 can include a cross protruding portion configured to couple with the locking mechanism 150.

The coupling assembly 140 can include or be coupled to a second motor. In some embodiments, the coupling assembly 140 can include or be coupled to the second motor. The coupling assembly 140 can initiate the rotation in response to receiving the signal. Accordingly, the guide wire 120, the cutting tool 160, the locking mechanism 150, or any portion between the proximal wire end 124 and the distal wire end 128 can rotate in tandem or synchronously with equivalent rotation or torque.

The locking mechanism 150 can include a hole, a path, a gap, or a hollow area to couple with the coupling assembly 140. The guide wire 120 can pass through locking mechanism 150 from a distal tube end 134 to the distal tube end 138 via the hollow area of the locking mechanism 150. In some embodiments, the locking mechanism 150 can include a protrusion on a portion of the locking mechanism 150 at, for example, the center, the perimeter, or between the center and the perimeter of the locking mechanism 150.

The locking mechanism 150 can be at the center or the middle of the cutting tool 160. In some embodiments, the locking mechanism 150 can enclose the guide wire 120 through, for example, a hollow portion of the locking mechanism 150. The cutting assembly 130 can traverse the guide wire 120 enclosed by the locking mechanism 150 through the lumen or duct 110. The locking mechanism 150 can include at least one hollow area, such as the center, the perimeter, or between the center and the perimeter. The hollow portion of the locking mechanism 150 can be of various shapes, such as a cross, a rectangle, a square, a circle, a triangle, or other geometric shapes. The locking mechanism 150 can include a thickness. The thickness can be 1, 2, 3, 4, 5, 6, 7, 8, 9, or 10 mm. The locking mechanism 150 can include an area. The area can be 1, 2, 3, 4, 5, 6, 7, 8, 9, or 10 millimeters squared. The cutting assembly 130 can include a protruding portion. The protruding portion can protrude a distance from the locking mechanism 150. The distance can be 100 nanometers, 500 nanometers, 1 millimeter. The distance can also be 2, 3, 4, 5, 6, 7, 8, 9, or 10 mm. In some embodiments, the locking mechanism 150 can include both at least one hollow portion and at least one protruding portion to facilitate engagement with the coupling assembly 140.

The locking mechanism 150 of the cutting assembly 130 can maneuver or be maneuvered to the coupling assembly 140 along the guide wire 120. The cutting assembly 130 can reach or position near the coupling assembly 140, such as 1 millimeter, 1 centimeter, or 1 inch from the coupling assembly 140. The locking mechanism 150, responsive or subsequent to approaching the coupling assembly 140, can be positioned or pulled towards the coupling assembly 140. The locking mechanism 150 can couple or attach to the coupling assembly 140 in response to a contact with the coupling assembly 140.

Referring specifically to FIGS. 1C and 1D, an illustration of the locking mechanism 150 coupling to the coupling assembly 140 can be shown. The cutting assembly 130 can transition from FIG. 1C to FIG. 1D by moving along the guide wire 120 towards the distal wire end 128. In some embodiments, the coupling assembly 140 is positioned at a distance from the distal wire end 128 of the guide wire 120. For instance, the cutting assembly 130 can couple with the coupling assembly 140 located a distance of a distal wire end 128 using the locking mechanism 150, as illustrated in FIG. 1C. The cutting assembly 130 can be maneuvered towards the coupling assembly 140, for example, by the operator manually inserting the cutting assembly 130 into the lumen or duct 110 or by an electrically operated device configured to maneuver the cutting assembly 130 along the guide wire 120. In some embodiments, the operator can push, thrust, or move the cutting assembly 130 along the guide wire 120. As illustrated in FIG. 1D, the cutting assembly 130 can couple to or lock with the coupling assembly 140. The cutting assembly 130 can receive an indication of the attached coupling assembly 140. The cutting assembly 130 can provide the indication to at least one external device connected to the cutting assembly 130, such as a display device, an audio device, the hand piece, or other signaling device. In some embodiments, the coupling assembly 140 can be an intermediate component for coupling the cutting assembly 130 with the guide wire 120.

The locking mechanism 150 can couple with the coupling assembly 140 via at least one coupling technique, such as friction fit, pin interconnection, torque fit, rotating coupling, snap ring, pin interconnect, magnets, friction fitting groove, or other coupling or fastening techniques to interlock or connect multiple components together. The protrusion of the locking mechanism 150 can couple with the coupling assembly 140. In some embodiments, the locking mechanism 150 can include both at least one hollow portion and at least one protruding portion to couple with the coupling assembly 140. For example, the cutting assembly 130 can traverse through the lumen or duct 110 using the guide wire 120. The cutting assembly 130 can reach the coupling assembly 140 located at a portion of the guide wire 120, such as at the distal wire end 128. The cutting assembly 130 can couple to the coupling assembly 140 using the locking mechanism 150 in contact with the cutting tool 160. In some embodiments, the coupling assembly 140 and the locking mechanism 150 can include a hollow portion or a protruding portion configured to couple between the two components. For example, the coupling assembly 140 can include opposite protruding portion or hollow portion to the locking mechanism 150, such as to enable friction fit, pin interconnect, twist lock, or other connection features.

Magnetic forces can also couple the coupling assembly 140 to the locking mechanism 150. In some embodiments, the coupling assembly 140 and the locking mechanism 150 can be composed of a magnetic material or a ferromagnetic material to provide a magnetic attraction between the two components. The ferromagnetic material can be iron, nickel, or cobalt. The locking mechanism 150 can attach to, pull in, or pull towards the coupling assembly 140 composed with at least one ferromagnetic material. In some embodiments, the locking mechanism 150 can be composed of the ferromagnetic material and the coupling assembly 140 can be composed of the magnetic material. The cutting assembly 130 can pull to the coupling assembly 140 when the locking mechanism 150 is within a range of the coupling assembly 140. The range can refer to a distance at which the locking mechanism 150 magnetically couples to the coupling assembly 140, such as 1, 2, 3, 4, 5, 6, 7, 8, 9, or 10 cm.

The cutting tool 160 can resect material 112 at from the lumen or duct 110. The cutting assembly 130, passing through the lumen or duct, can cut, remove, shaves or debride the material 112 using the cutting tool 160. In some embodiments, the cutting tool 160 debrides or cuts the material 112 from the lumen or duct 110. The cutting tool 160 can cut the material 112 into small enough pieces, which the cutting assembly 130 can retrieve such that the cutting assembly 130 collects the debrided material 112 without removing the cutting assembly 130 from the lumen or duct 110. In some embodiments, responsive to the cutting tool 160 debriding the material 112 into debrided materials, the cutting assembly 130 can pull in, withdraw, or pump out the debrided materials 112 from the lumen or duct 110. The debrided materials 112 can be collected into the groove and traverse down from a distal end of the cutting tool 160 to a proximal end of the cutting tool 160 for collection of the debrided materials 112. The cutting tool 160 can pull the debrided materials from the distal tube end 138 to the proximal tube end 134 of the cutting assembly 130.

The cutting tool 160 can capture or collect the debrided materials 112 from the lumen or duct 110 using the grooves or sockets engraved within the cutting tool 160. Debriding can include any action involving detaching the material 112 or a portion of the material 112 from the lumen or duct 110. Accordingly, actions, including but not limited to, extracting, dissecting, cutting, shredding, slicing, shattering, either entirely or partially, are also examples of debriding. In some embodiments, the cutting tool 160 is manually operated or can utilize any other means of debriding material 112 such that cutting tool 160 retrieves the debrided material 112 from the lumen or duct 110, such as via the aspiration channel 222, described below. The cutting tool 160 can rotate at various speeds to the cut the material 112, such as 1000 rotations per minute ("RPM"), 5,000 RPM, 10,000 RPM, 20,000 RPM, 30,000 RPM, 40,000 RPM, or 50,000 RPM.

The cutting tool 160 can include snips, blades, saws, or any other sharp tools. The cutting tool 160 can include at least one type of cutting, dissecting, or extracting mechanism, such as a fan, an axial cutter, a drill, a hook, a reamer, a miller cutter, or other cutting tools or devices. The cutting tool 160 can include a spiral groove traversing from the distal end of the cutting tool 160 to the proximal end of the cutting tool 160, configured to pass the debrided materials 112 along the spiral groove. The cutting tool 160 can be composed of one or more materials, such as steels, plastics, carbon fibers, titanium, aluminums, metals, or other alloys for cutting the material 112. In some embodiments, the cutting tool 160 includes a radiopaque cutting tip.

The cutting tool 160 can couple to or be adjacent to the distal tube end 138 of the cutting assembly 130. The cutting tool 160 can include a proximal end, located similar to the proximal wire end 124, and a distal end, located at the distal tube end 134 or the tip of the cutting assembly 130. The cutting tool 160 can include a length. In some embodiments, the length is similar to the cutting assembly 130. In some embodiments, the length is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 cm.

Now referring to FIG. 1C, the cutting tool 160 can include the fan blades 165a-c (generally referred to as fan blade 165). The fan blades 165 can be composed of one or more materials for cutting or dissecting the material 112, such as a metal, a titanium, an aluminum, or alloy. The cutting tool 160 can include one or more blades, such as three blades as shown in FIG. 1C. In some embodiments, the cutting tool 160 includes 1, 2, 3, 4, 5, 6, 7, 8, 9, 10, 20, 30, 40, 50, 60, 70, 80, 90, or 100 fan blades 165.

Figure 3A:
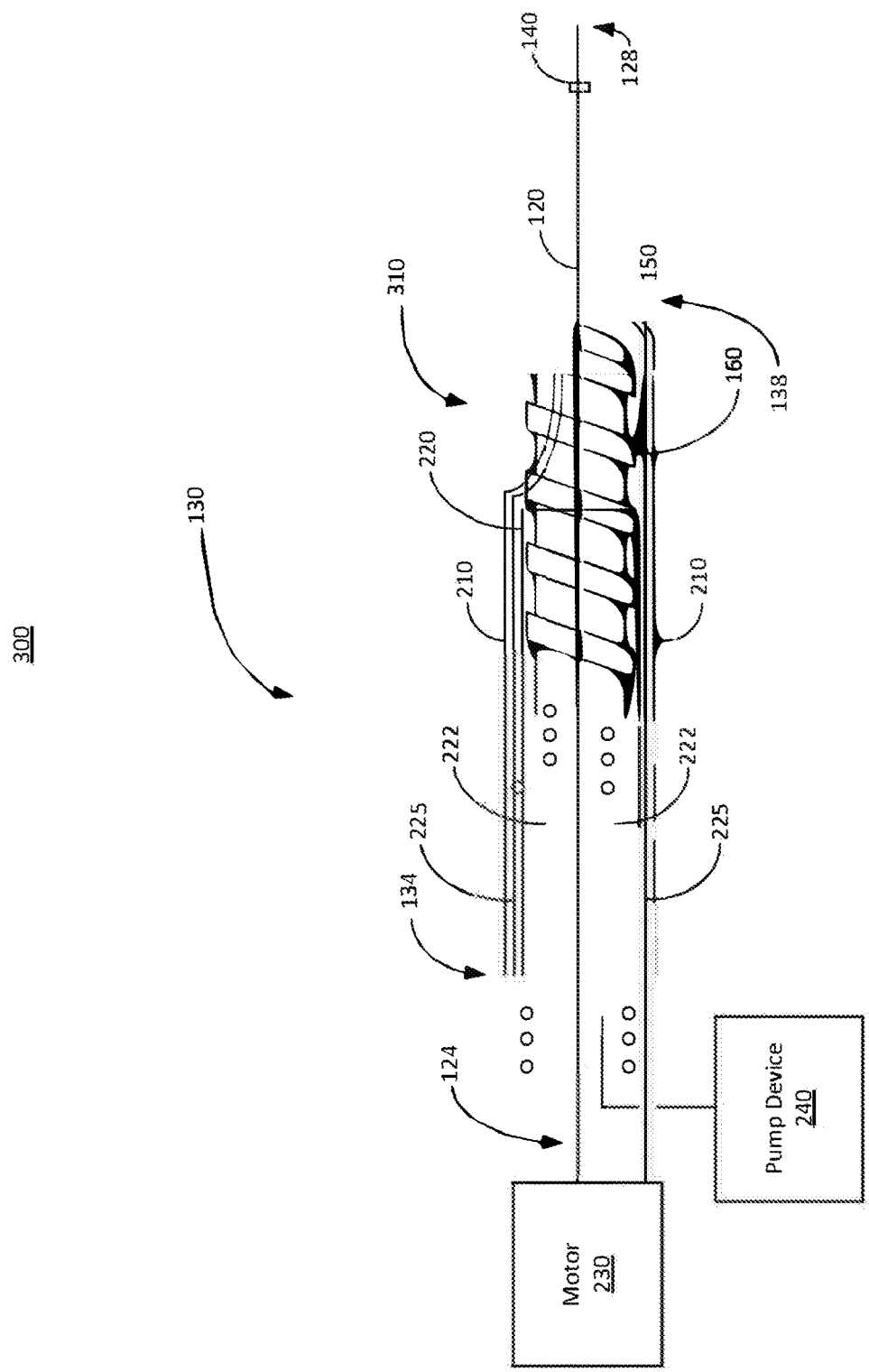
FIG. 3A shows a side cross-sectional view of the material removal system including the cutting tool, the guide wire, the motor, and the coupling assembly according to embodiments of the present disclosure.

The cutting tool 160 can also be exposed on a side of the outer cannula 210, such as at a cutting window 310 as shown in FIG. 3A, for tangential or side cutting with respect to the movement of the guide wire 120 or the cutting assembly 130. The cutting tool 160 couples to the outer cannula 210 of the cutting assembly 130, such as a groove within the outer cannula 210 for rotating the cutting tool 160. In some embodiments, the cutting tool 160 can be a distance from the inner cannula 220, such as 1 millimeter, 2 millimeters, or 3 millimeters from the inner cannula 220. In some embodiments, the cutting assembly 130 does not include the inner cannula 220, and only includes the cutting tool 160 enclosed by the outer cannula 210. The cutting tool 160 can include the locking mechanism 150.

The cutting tool 160 can be rotated after the locking mechanism 150 couples to the coupling assembly 140. The cutting tool 160 can include the locking mechanism 150. The cutting tool 160 can rotate with the locking mechanism 150. The cutting tool 160 can perform axial cutting, such as by including a linear actuator that couples with the guide wire 120 to be driven along an axis of the cutting assembly 130 responsive to rotation of the guide wire 120. In some embodiments, the cutting tool 160 can be manually actuated such that the cutting tool 160 can be operated through the translation of mechanical forces exerted by the operator or automatically actuated, using a turbine, the motor 230, or any other force generating component to actuate the cutting tool 160.

Referring to FIGS. 2A-D, a material removal system 200 can include the guide wire 120, the cutting assembly 130, a motor 230, and a pump device 240. The material removal system 200 can be the material removal system 115 shown in FIG. 1. The cutting assembly 130 includes the cutting tool 160, the locking mechanism 150, an outer cannula 210, an inner cannula 220, an aspiration channel 222, and an irrigation channel 225. In some embodiments, the outer cannula 210 can optionally include a socket 215. In some embodiments, a hand piece (not shown) can couple to the guide wire 120, the cutting assembly 130, the motor 230, and the pump device 240. The operator can use the hand piece to control the guide wire 120, the cutting assembly 130, the motor 230, the pump device 240, or any other external devices. In some embodiments, the hand piece can be configured to control the components simultaneously, such that the cutting tool 160 is rotating while the pump device 250 provides suction and irrigation substance. In some embodiments, the hand piece can control each component independently, such as only initiating the rotation of the motor 230 or only initiating suction using the pump device 240.

The outer cannula 210 can be a cover, an outer tube, a shell, or a main body of the cutting assembly 130. The outer cannula 210 can enclose the distal tube end 138 or the tip of the cutting assembly 130. The outer cannula 210 can includes an opening, such as the cutting window 310, at the distal tube end 138 of the cutting assembly 130. A portion of the radial wall of the outer cannula 210 can define the opening that extends around a portion of the radius of the outer cannula 210. In some embodiments, the operator can receive or retrieve debrided materials from cutting the material 112.

The outer cannula 210 can be shaped or formed to, for example, a cylinder, a prism, a cone, or other shapes. The outer cannula 210 can be flexible. The outer cannula 210 can bend and flex to any degree. In some embodiments, the outer cannula 210 can bend and flex to 10, 20, 30, 40, 50, 60, 70, 80, 90, 100, 110, 120, 130, 140, 150, 160, 170, or 180 degrees. The outer cannula 210 can include a thickness. The thickness can be 10 nanometers, 20 nanometers, 1 millimeter, 2 millimeters, 3 millimeter, 4 millimeters, or 5 millimeters. The outer cannula 210 can include a width. The width can be 1 millimeter, 2 millimeters, 3 millimeter, 4 millimeters, 5 millimeters, or 1 centimeter. The outer cannula 210 can include a length. The length can be 1 meters, 2 meters, 3 meters, 4 meters, 5 meters, 6 meters, 7 meters, 8 meters, 9 meters, 10 meters, 50 meters, 100 meters, etc. The outer cannula 210 can include a cross-sectional area, such as 0.6 millimeters squared, 1 millimeters squared, 1.9 millimeters squared, etc. The outer cannula 210 can be composed of materials, such as metal, steel, plastic, rubber, glass, carbon fiber, titanium, aluminum, or other alloys.

Figure 2A:
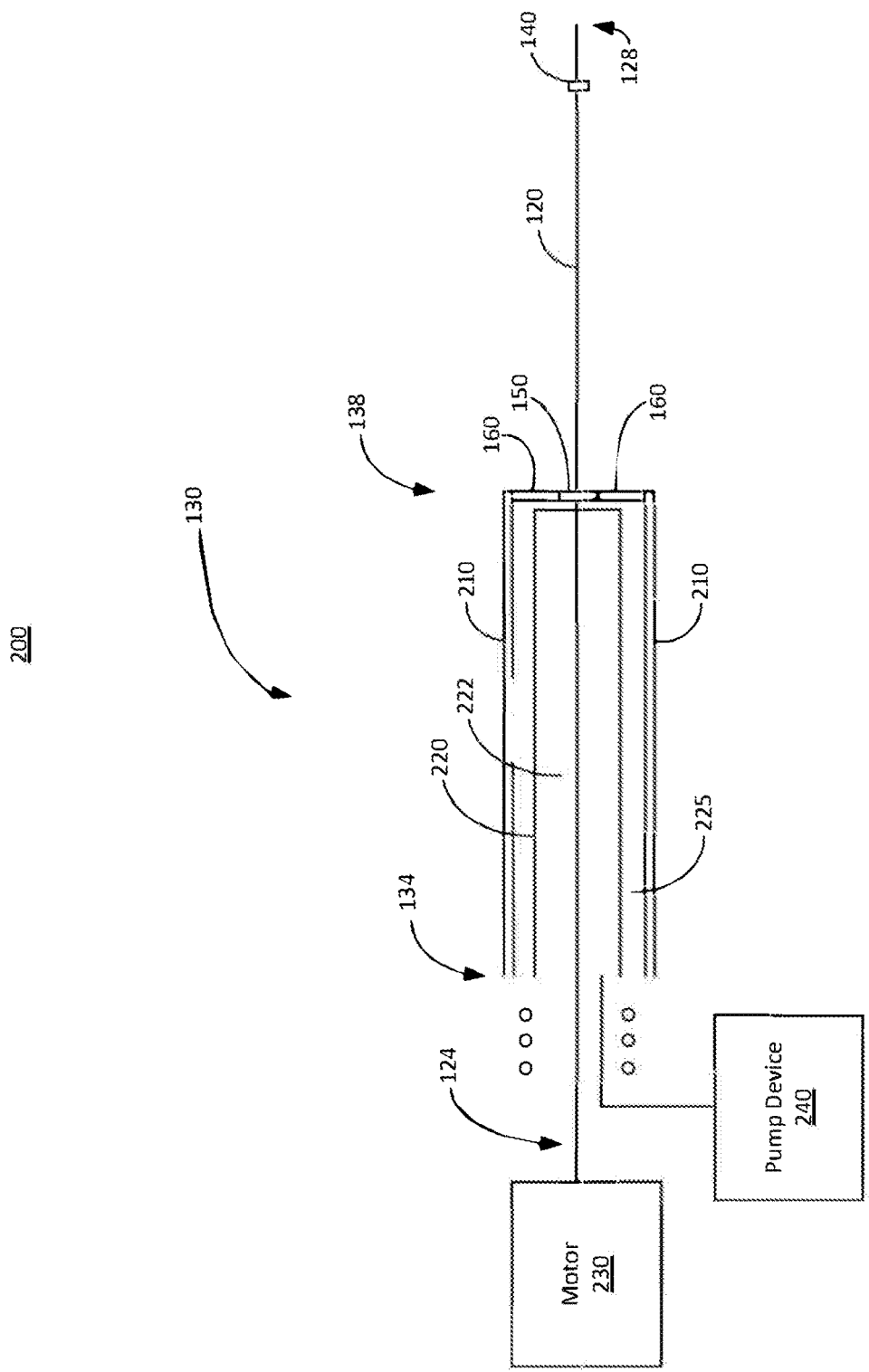
FIG. 2A shows a top cross-sectional view of the guide wire, the cutting assembly, the motor, and the coupling assembly according to embodiments of the present disclosure.
Figure 2B:
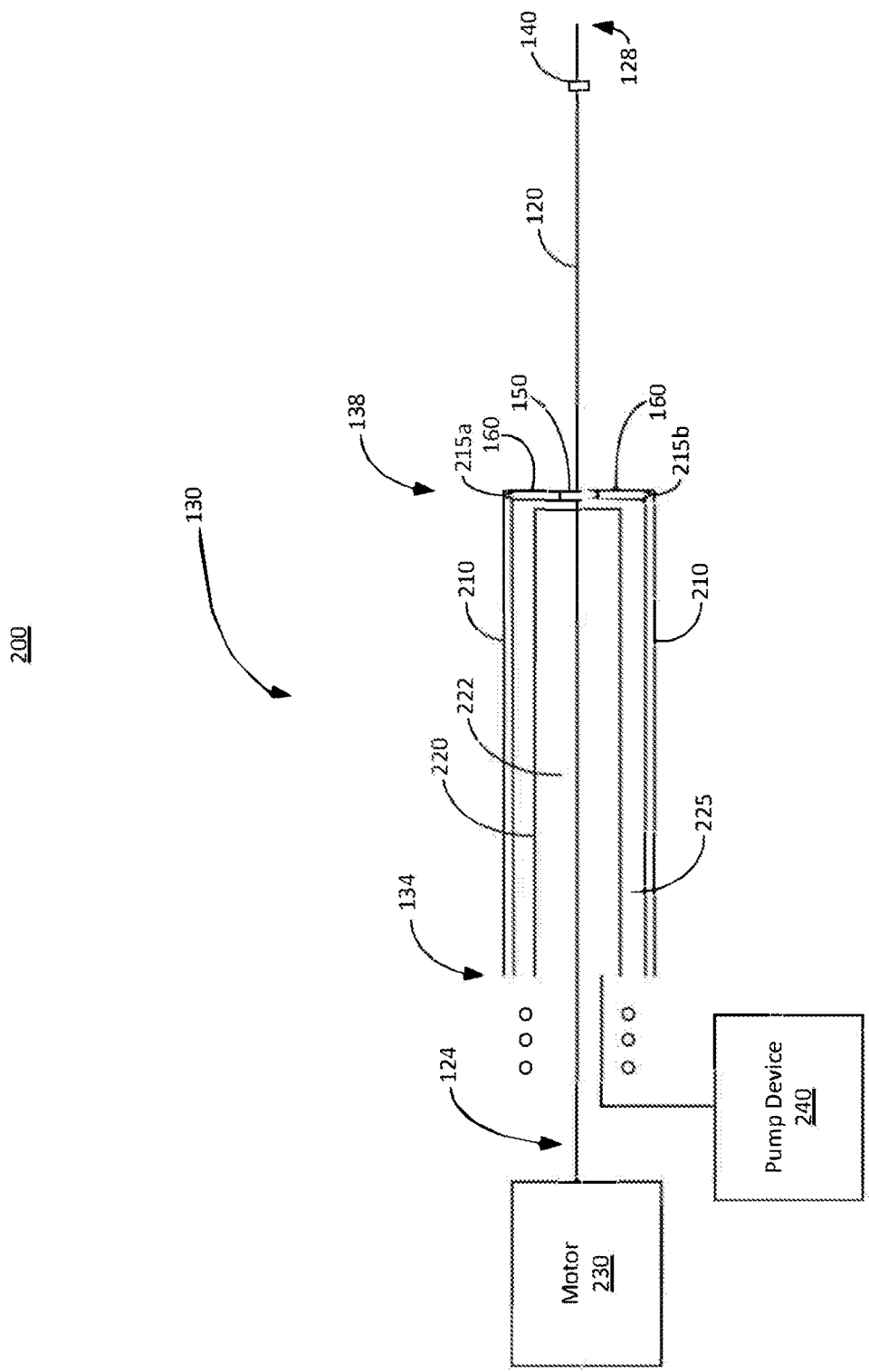
FIG. 2B shows a top cross-sectional view of the guide wire, the cutting assembly, the motor, and the coupling assembly according to embodiments of the present disclosure.

The inner cannula 220 can rotate relative to the outer cannula 210, for example, by using a groove, a socket, or a bolt included in outer cannula 210 or on the inner cannula 220. Referring now to FIG. 2B, the outer cannula 210 can optionally include the socket 215 coupling the cutting tool 160 to the outer cannula 210. The cutting tool 160 can rotate independent to the outer cannula 210. For example, the motor 230 can actuate a rotation to the guide wire 120 to exert a rotation to the coupling assembly 140 coupled to the cutting tool 160. The cutting tool 160 can rotate within the socket 215 of the outer cannula 210. The socket 215 can facilitate the positioning of the cutting tool 160 within the cutting assembly 130, such that the cutting tool 160 does not depart or separate from the distal tube end 138 of the cutting assembly 130 during rotation.

Referring back to FIGS. 2A-D, the outer cannula 210 can at least partially surround the inner cannula 220. In some embodiments, the inner cannula 220 resects any material suctioned into or otherwise entering the opening of the distal tube end 138. The inner cannula 220 can include an opening at the distal tube end 138 of the cutting assembly 130 such that material resected by the cutting tool 160 enters via the opening at the distal tube end 138. A distal tube end 138 of the inner cannula 220 can include the cutting section while a proximal wire end 124 of the inner cannula 220 can be open such that material 112 entering the distal tube end 138 of the inner cannula 220 via the cutting section can pass through the proximal wire end 124 of the inner cannula 220. In some embodiments, the guide wire 120 attaches to the inner cannula 220 to cause the inner cannula 220 to rotate along the longitudinal axis of the inner cannula 220 with the cutting tool 160. If the outer cannula 210 does not attach to the inner cannula 220 or the guide wire 120, the inner cannula 220 can rotate relative to the outer cannula 210. In some embodiments, the inner cannula 220 can rotate relative to the outer cannula 210 along a generally longitudinal axis, providing more stability to the inner cannula 220 during rotation.

The inner cannula 220 can include a length similar to or less than the outer cannula 210. The length can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 cm. The inner cannula 220 can be designed to facilitate debriding one or more materials 112 and removing the debrided materials 112 associated in a single operation. The inner cannula 220 can be disposed within the outer cannula 210. The inner cannula 220 can couple with the outer cannula 210 of the cutting assembly 130. The inner cannula 220 can be composed of a similar material as the outer cannula 210. The inner cannula 220 can be flexible, similar to the outer cannula 210.

The inner cannula 220 can be coupled to at least one external device, such as the pump device 240. The inner cannula 220 can provide a path to pull, draw, or drag one or more substances including the material 112 away from the lumen or duct 110 using the pump device 240. For example, the operator can insert the cutting assembly 130 into the lumen or duct 110. The cutting assembly 130 can maneuver to the material 112 using the guide wire 120. The cutting assembly 130 can provide or propel the irrigation substance, such as water or air to the lumen or duct 110 using an pump. The cutting assembly 130 can pull, collect, or receive a portion of the material 112 (or debrided material 112), using the pump device 240. The collected material 112 can transfer through the inner cannula 220 to an external collection device (not shown) for inspection or collection. In some embodiments, the inner cannula 220 is a component separate from the cutting assembly 130 or the outer cannula 210.

In some embodiments, the inner cannula 220 can be equipped with an injectable dye component through which the operator can use to determine the extent of narrowing under fluoroscopic guidance or to mark a particular region within the lumen or duct 110. In other embodiments, the operator can mark a particular region with the cutting tool 160, without the use of an injectable dye.

In some embodiments, the inner cannula 220 can include multiple tubes, such as a first inner cannula and a second inner cannula. The first inner cannula can couple with or connect to a first pump device. The second inner cannula can couple with or connect to a second pump device. The first pump device can connect to a reservoir including the irrigation substances, such as chemical compounds or gases. The first pump device can expel the irrigation substance into the lumen or duct 110. The second pump connects to a collection device, such as a different reservoir. The second pump device can retrieve, pull, or collect the material 112 from the lumen or duct 110 to a different reservoir for storage. For example, the operator can guide the cutting assembly 130 along the guide wire 120 to the material 112 within the lumen or duct 110. The cutting assembly 130 can couple to the coupling assembly 140. The motor 230 can initiate a rotation of the guide wire 120. The coupling assembly 140 can initiate the rotation in response to the rotation of the motor 230. The cutting tool 160 can rotate with the coupling assembly 140 to debride the material 112 in the lumen or duct 110. The first inner cannula can provide air and water to assist the debriding process of the cutting tool 160 using the first pump device. The second inner cannula can retrieve the debrided material 112 from the lumen or duct 110 using the second pump device. In some embodiments, the first pump device and the second pump device can provide the irrigation substance and retrieve material 112 synchronously or concurrently.

The inner cannula 220 can be hollow such that an inner wall of the inner cannula 220 can define at least a portion of the aspiration channel 222. In some embodiments, the outer wall of the guide wire 120 can be configured to define another portion of the aspiration channel 222 that is fluidly coupled to the portion of the aspiration channel 222 defined by the inner wall of the inner cannula 220 of the cutting assembly 130. In some embodiments, the inner cannula 220 can include a lining within which the guide wire 120 is disposed. In some embodiments, the lining surrounding the guide wire 120 also defines the aspiration channel 222. The lining can be a barrier between the guide wire 120 and the aspiration channel 222. Accordingly, the lining can allow the aspiration channel 222 to maintain a suction force throughout the length of the aspiration channel 222 by preventing air from escaping or entering through the guide wire 120 or the inner cannula 220.

The aspiration channel 222 can extend through the length of the cutting assembly 130. A proximal end of the aspiration channel 222 at the distal tube end 138 of the cutting assembly 130 can receive a suction force. The suction force causes at least one material 112 to be introduced into the opening of the outer cannula 210 adjacent to the distal end of the aspiration channel 222, which can then be cut by the inner cannula 220 of the cutting assembly 130. The suction force can suction, retrieve, pull in, or otherwise withdraw the material 112 at a distal end of the aspiration channel 222 from the lumen or duct 110, and pull the material 112 through the aspiration channel 222 to the proximal end of the aspiration channel 222. As such, the size of the opening at the distal tube end 138 can be determined based in part on the size of the aspiration channel 222 defined by the inner circumference of the outer cannula 210.

The inner cannula 220 can have a spacing, an area, or a gap with the outer cannula 210. In some embodiments, the spacing includes a gap of, for example, 0.1, 0.2, 0.3, 0.4, 0.5, 0.6, 0.7, 0.8, 0.9, 1.0, 2, 3, 4, or 5 mm. In some embodiments, the outer cannula 210 can couple to the cutting tool 160, such as via a groove of the outer cannula 210 located at a distal tube end 138 of the outer cannula 210. In some embodiments, the inner cannula 220 can reside between the outer cannula 210 and the cutting tool 160, such that the inner cannula 220 encloses the cutting tool 160. In some embodiments, the inner cannula 220 can rotate about a longitudinal axis of the inner cannula 220 and relative to the outer cannula 210. For example, the guide wire 120 can cause the inner cannula 220 to rotate, via rotation of the coupling assembly 140 coupled to the locking mechanism 150, independently and relative to the outer cannula 210. The spacing between the outer cannula 210 and the inner cannula 220 can define the irrigation channel 225.

The irrigation channel 225 can provide irrigation substance to the lumen or duct 110. In some embodiments, the irrigation channel 225 can provide the irrigation substance to the aspiration channel 222. The irrigation substance can be stored in a repository or a container (not shown), which can be external or internal to the cutting assembly 130. In some embodiments, the cutting assembly 130 can receive the irrigation substance through an opening, as described in more details in FIG. 4. An external device, such as the pump device 240, can push the substance through the irrigation channel 225. The operator can apply the irrigation substance to the lumen or duct 110. The operator can apply the irrigation substance to unblock an opening located in the lumen or duct 110 (e.g. blocking a damaged portion of the lumen or duct 110). The operator can apply the irrigation substance to provide an ointment or other medication to the lumen or duct 110 to facilitate the healing process to damaged portions of the lumen or duct 110. In another example, the operator can pump at least a liquid or a gas into the irrigation channel 225 to facilitate the debriding process of the material 112 located in the lumen or duct 110.

The cutting assembly 130 can define the irrigation channel 225. In some embodiments, the inner wall of the outer cannula 210 can define the irrigation channel 225. In some embodiments, the outer wall of the inner cannula 220 can define the irrigation channel 225. In some embodiments, the outer wall of the inner cannula 220 and the inner wall of the outer cannula 210 can define a portion of the irrigation channel 225. In some embodiments, the irrigation channel 225 can extend from the irrigation entry port to the opening of the outer cannula 210, for example, at the distal tube end 138. In some embodiments, the inner wall of the inner cannula 220 can serve to prevent any material 112 passing through the aspiration channel 222 from escaping through the walls. In some embodiments, the outer wall of the inner cannula 220 can prevent the irrigation substance from passing through the irrigation channel 225 to flow into the aspiration channel 222 through the walls of the inner cannula 220. In some embodiments, the irrigation channel 225 has similar functionalities as described for the aspiration channel 222, such as for suctioning material 112.

The motor 230 of the material removal system 200 can couple to the guide wire 120 to rotate the guide wire 120. The motor 230 can provide a rotation, a torque, or a signal to the guide wire 120. The motor 230 can provide the rotation to the proximal wire end 124 of the guide wire 120. The coupling assembly 140 can receive the torque traversed from the proximal wire end 124 to the distal wire end 128 of the guide wire 120. The locking mechanism 150 can receive a rotational force from the coupling assembly 140. For example, the locking mechanism 150 can receive the rotational force from the coupling mechanism when the motor 230 (i.e. manually or electrically powered by the operator) initiates or exerts a rotation to the guide wire 120.

The motor 230 can rotate the coupling assembly 140 by rotating the guide wire 120. The guide wire 120 can transmit the torque received at the proximal wire end to the coupling assembly 140, which in turn transmits the torque to the locking mechanism 150 of the cutting assembly 130 to cause the cutting tool 160 of the cutting assembly 130 to rotate. The motor 230 can initiate a rotation of the guide wire 120. In response, the coupling assembly 140 can subsequently rotate. For example, the motor 230 can initiate a 30 degrees rotation of the guide wire 120. In response, the coupling assembly 140 can rotate 30 degrees. In some embodiments, the motor 230 can initiate a rotation to the proximal wire end 124 of the guide wire 120. The torque provided to the proximal wire end 124 of the guide wire 120 can cause rotation of the distal wire end 128. The coupling assembly 140, responsive or subsequent to the initiated rotation by the motor 230, can rotate at or a distance from the distal wire end 128 of the guide wire 120. For example, the motor 230 can initiate a 60 degrees rotation to the proximal wire end 124 of the guide wire 120. The torque provided to the proximal wire end 124 of the guide wire 120 can cause a corresponding 60 degrees of rotation to the distal wire end 128. The coupling assembly 140, responsive or subsequent to the initiated rotation by the motor 230, can provide a 60 degrees rotation at or a distance from the distal wire end 128 of the guide wire 120.

The motor 230 can transmit a signal including information of the rotation or the torque to the coupling assembly 140 via the guide wire 120. The guide wire 120 can be similar to a cable or a wire configured to transmit or receive signals. The coupling assembly 140 can include a controller configured to receive a signal for initiating a rotation. The coupling assembly 140 can to receive the signal indicating a rotation, a torque, or other information provided by the motor 230. For example, the operator can manually or actuate the motor 230 to transmit a signal to the coupling exert a rotation of 90 degrees. The motor 230 can transmit the signal be transmitted to the coupling assembly 140. The coupling assembly 140 can exert a rotation of 90 degrees in response to the received signal, similar to the motor 230.

The equivalent rotation of the motor 230 and the coupling assembly 140 can provide an improved accuracy, cutting precision, control, and power consumption relating to use of the cutting tool 160. The rotation by the coupling assembly 140 matching the rotation of the motor 230 can facilitate control of the cutting tool 160 by providing even distribution of power, rotation, or torque from the proximal wire end 124 to the distal wire end 128. Without the coupling assembly 140 fixed to the guide wire 120, the cutting tool 160 can rotate or provide a torque greater than or less than the motor 230, which can introduce less precision, and more power consumption to rotate a specific degree. For example, without equivalent rotation between the proximal wire end 124 and the distal wire end 128 of the guide wire 120, the motor 230 can rotate 30 degrees, and the cutting tool 160, located at the distal wire end 128, can rotate 15 degrees. In some embodiments, the difference between the rotation at the proximal wire end 124 and the distal wire end 128 is associated with the length of the guide wire 120 and the cutting assembly 130. In such embodiments, and as an example, the motor 230 can provide a 90 degrees rotation to the proximal tube end 134, and if the cutting tool 160 is located 5 meters from the proximal tube end 134, the cutting tool 160 can initiate 60 degrees of rotation. In further example, if the cutting tool 160 is located 10 meters from the proximal tube end 134, the 90 degrees rotation exerted by the motor 230 can convert to 30 degrees of rotation by the cutting tool 160.

The motor 230 can supply electric current to the guide wire 120. The motor 230 can supply electric current to the proximal wire end 124 of the guide wire 120. The current in the guide wire 120 can power the sensors in the guide wire 120. In some embodiments, a separate conduit passing through the tubing or a channel of the cutting assembly can carry an electrical wire to provide power to the guide wire 120. The current from the power source can magnetize the coupling assembly 140. The coupling assembly 140 will couple to the locking mechanism 150 of the cutting assembly 130 to the magnetized guide wire 120. In some embodiments, the locking mechanism 150 and the coupling assembly 140 form an electrical connection such that electric current in the guide wire 120 flows to the coupling assembly 140 and to the locking mechanism 150. In some embodiments, the magnetic field terminates responsive to blocking the electrical power from the motor 230 to terminate the current flowing to the guide wire 120 composed with the magnetic material. When the guide wire 120 is demagnetized, the coupling assembly 140 will de-couple from the locking mechanism 150 of the cutting assembly 130.

The motor 230 can supply electric current to the cutting assembly 130. The motor 230 can supply electric current to the proximal tube end 134 of the cutting assembly 130. In some embodiments, the cutting assembly 130 receives electric current from the guide wire 120 via the locking mechanism 150. The current in the cutting assembly 130 can power the cutting assembly 130. In some embodiments, the current in the cutting assembly 130 can power the cutting tool 160. In some embodiments, the current in the cutting assembly 130 can power sensors in the cutting assembly 130. In some embodiments, the motor 230 pushes, thrusts, or moves the cutting assembly 130 along the guide wire 120. The motor 230 can be external to the cutting assembly 130.

The operator can manually or electrically operate the motor 230. In some embodiments, the hand piece can include a variable valve to control the amount of power applied by the motor 230. The motor 230 can connect to a power source, configured for receiving electrical energy. The motor 230 can be a hydraulic, pneumatic, electric, or piezoelectric. The component of the motor 230 can include, for example, a rotor, a bearing, a stator, and a motor control. In some embodiments, the motor 230 is part of the material removal system 200 such that the material removal system 200 is a standalone device, tool, or component. In some embodiments, the motor 230 can operate using alternating current ("AC") or direct current ("DC"). The motor 230 can convert the electrical energy into mechanical energy for initiating at least one component or mechanism inside the motor 230. In some embodiments, actuation of the motor 230 automatically actuates the pump device 240 to retrieve the resected material 112.

The pump device 240 can retrieve, extract, or collect debrided material 112 from the lumen or duct 110. The pump device 240 can pull, draw, or drag the material 112 from the lumen or duct 110 via the aspiration channel 222. The pump device 240 initiate a suction feature or force to retrieve debrided materials 112 or the irrigation substance from the lumen or duct 110 at the distal tube end 138, passing the irrigation substance through the aspiration channel 222 to the proximal tube end 134. The pump device 240 can also pull liquid, fluid, or gas within the lumen or duct 110. For example, the cutting assembly 130 can reach the material 112 and initiate a debriding process to cut or dissect the material 112 from the lumen or duct 110 into small pieces or debrided materials 112. The pump device 240 can initiate in response to debriding the material 112. Accordingly, the debrided materials 112 can be aspirated, suctioned, or pulled into the inner cannula 220 of the cutting assembly 130 for retrieval or extraction of the material 112. In some embodiments, pump device 240 can include a collection cartridge or a repository for storing the debrided materials, resected material, or the irrigation substance retrieved from the lumen or duct 110 using the pump device 240. In some embodiments, the collection cartridge fluidly couples to the proximal end of the aspiration channel 222.

In some embodiments, the pump device 240 can provide the irrigation substance to the lumen or duct 110 via a first inner cannula, and retrieve at least one material 112 from the lumen or duct 110 via a second inner cannula. In some embodiments, the cutting assembly 130 does not include the pump device 240. Additionally, the pump device 240 can be configured to provide the irrigation substance or into the lumen or duct 110 towards the material 112.

The pump device 240 can push, provide, transmit, or introduce one or more substances into the lumen or duct 110. For instance, the pump device 240 can provide gases, liquids, or other chemical compounds into the lumen or duct 110. The provided substances can facilitate a debriding process of the material 112. The provided substances can also provide a treatment solution to a damaged portion of the lumen or duct 110. For example, the lumen or duct wall 110 can include a narrowing. The pump device 240 can provide a coating substance or compound to block, cover, or repair the narrowing. The pump device 240 can pull the irrigation substance from a storage and push the irrigation substance into the lumen or duct 110. In some embodiments, two pump devices can be included, such as one for suctioning via the aspiration channel 222 and one to provide substance via the irrigation channel 225.

The pump device 240 can provide the irrigation substance via the guide wire 120. In some embodiments, the proximal wire end 124 can be connected to the pump device 240 configured to provide the irrigation substance. The guide wire 120 can include a delivery channel (not shown) configured to receive the irrigation substance at the proximal wire end 124 and release the irrigation substance at the distal wire end 128. The irrigation substance can irrigate the lumen or duct 110. In some embodiments, the irrigation substance can irrigate the material 112 as the guide wire 120 navigates within the lumen or duct 110 to the material 112.

The pump device 240 can provide the irrigation substance via the irrigation channel 225. The pump device 240 can control the flow of the irrigation substance through the irrigation channel 225 of the cutting assembly 130. In some embodiments, the pump device 240 can provide a push feature to expel, transmit, or otherwise provide the irrigation substance into the lumen or duct 110 via the cutting assembly 130. The pump device 240 can provide the irrigation substance via the irrigation channel 225. The pump device 240 can couple to a proximal tube end 134 of the cutting assembly 130. In some embodiments, pump device 240 can connect to the aspiration channel 222 via the proximal tube end 134. The pump device 240 can connect to the irrigation channel 225 of the cutting assembly 130. The pump device 240 can include components. The components can include a casing, an impeller, a backing plate, a shaft, and a shaft seal, for example. The pump device 240 can be external to the cutting assembly 130. The operator can initiate the pump device 240 by a signal or a mechanical trigger. In some embodiments, the hand piece can include a variable valve to control the amount of irrigation of suction supplied by the pump device 240.

Figure 3C:
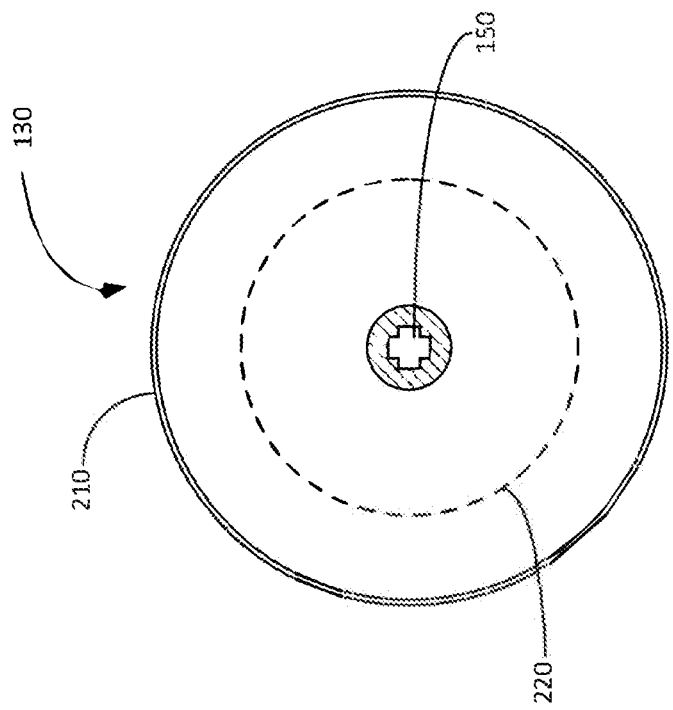
FIG. 3C shows a front view of the material removal system including the cutting tool according to embodiments of the present disclosure.
Figure 3B:
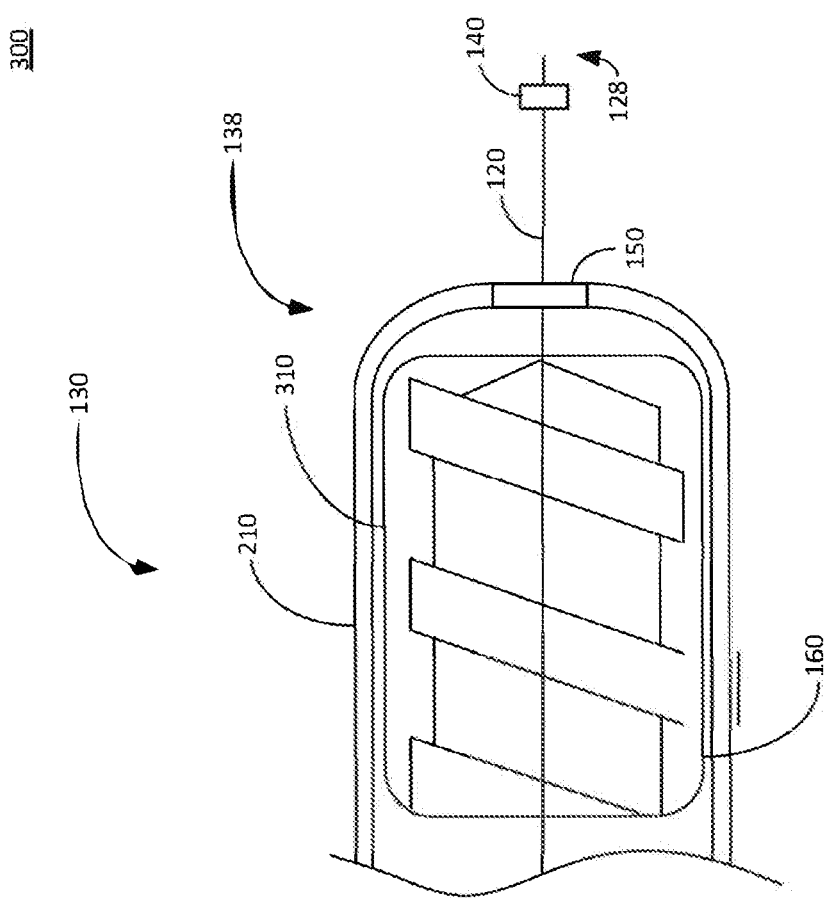
FIG. 3B shows a top cross-sectional view of the material removal system including the cutting tool according to embodiments of the present disclosure.

Referring to FIGS. 3A-C, shown is a material removal system 300 with various views of the cutting assembly 130 having a cutting window 310. The following description describes the material removal system 300 in detail, in addition to the descriptions and examples of FIGS. 1 and 2.

The cutting window 310 can receive the material 112 in the lumen or duct 110. The cutting window 310 can positioned at a side of the outer cannula 210. The cutting window 310 enables tangential or side cutting of material 112 with respect to the movement of the guide wire 120 or the cutting assembly 130. In some embodiments, the outer cannula 210 can include the cutting window 310. The cutting window 310 can include a hollow structure with a shape, such as a circle, an oval, a rectangle, or other geometric shape for expositing the cutting tool 160. The cutting window 310 can include a diameter. The diameter can be 1 millimeter, 2 millimeters, 3 millimeters, 4 millimeters, or 5 millimeters. The cutting window 310 can include a cut out, which can be a portion of the cutting assembly 130. For example, the cutting window 310 can include a 0.4 millimeters cut out.

The cutting window 310 can be configured to enable the cutting tool 160 to cut, dissect, or debride the material 112 in the lumen or duct 110 via the cutting window 310. For example, the cutting assembly 130 couples to the coupling assembly 140. The motor 230 can initiate a rotation of the guide wire 120. The coupling assembly 140 can rotate equivalent to the rotation of the motor 230 or the proximal wire end 124. The cutting tool 160 fixed to the locking mechanism 150 can rotate with the coupling assembly 140 to initiate a debriding process. For example, the cutting assembly 130 can initiate the debriding or cutting process by rotating the cutting tool 160 through the material 112 to receive the material 112 in the cutting window 310 of the cutting assembly 130. The cutting assembly 130 can receive one or more portions of the material 112 via the cutting window 310, and debride the material 112 using the cutting tool 160. The pump device 240 can suction or pull the debrided materials 112 from the lumen or duct 110 through the inner cannula 220.

Figure 4:
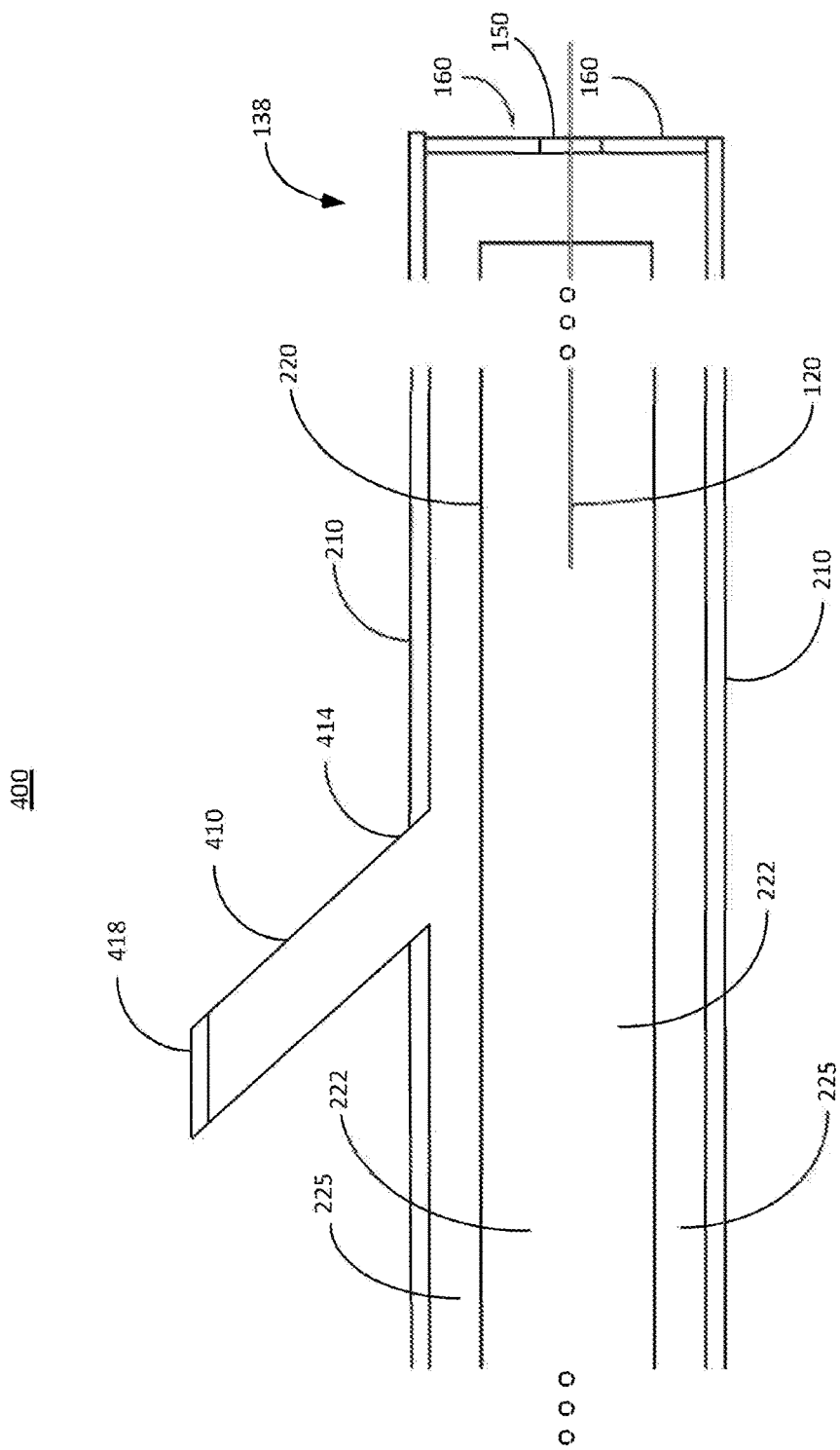
FIG. 4 shows an enlarged cross-sectional view of the material removal system according to embodiments of the present disclosure.

Referring to FIG. 4, shown is an enlarged cross-sectional view of a material removal system 400. The following description, in addition to the descriptions and examples of FIGS. 1-3, describes the material removal system 400 in detail. The cross-sectional view can illustrate a portion of the cutting assembly 130. Specifically, the cutting assembly 130 can include a lavage connector 410 having a proximal connector end 414 and a distal connector end 418.

The lavage connector 410 can be a tubular member for providing irrigation substance to the cutting assembly 130. A gap between an outer wall of the inner cannula 220 and the inner wall of the outer cannula 210 can define a portion of the irrigation channel 225. Irrigation substance can flow through the portion from the lavage connector 410 from the proximal connector end 414 to the distal connector end 418 through the irrigation channel 225 portion towards the cutting tool 160. The irrigation substance from the irrigation channel 225 can subsequently disperse or provide the irrigation substance into the lumen or duct 110. The irrigation substance can irrigate the material 112. The inner cannula 220 can define a portion of the aspiration channel 222 through which excised or resected material and the irrigation substance can flow from the cutting tool 160 towards proximal tube end 134 of the cutting assembly 130.

The lavage connector 410 can be a Y port extending from the outer cannula 210 at an angle with the distal tube end 138. The angle can be 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, or 180 degrees. In some embodiments, the lavage connector 410 can be located external to the portions of the cutting assembly 130 inserted into the lumen or duct 110. In some embodiments, the outer cannula 210 can extend from the distal connector end 418 of the lavage connector 410 to a proximal tube end 134 of the cutting assembly 130, which can be external to the lumen or duct 110. In some embodiments, the lavage connector 410 can be an isolated component of the cutting assembly 130, such that the lavage connector 410 does not rotate as the motor 230 actuate a rotation to the guide wire 120. The lavage connector 410 can provide a stable opening for external irrigation substance to enter into irrigation channel 225.

The proximal connector end 414 of the lavage connector 410 can couple the lavage connector 410 to an opening of the outer cannula 210. The lavage connector 410 can couple with an inner wall of the outer cannula 210 at the proximal connector end 414. In some embodiments, the distal connector end 418 of the lavage connector 410 can be press fit into a proximal tube end 134 of the outer cannula 210 of the cutting assembly 130. In some embodiments, the proximal connector end 414 of the lavage connector 410 can connect to with the proximal tube end 134 of the cutting assembly 130.

The distal connector end 418 of the lavage connector 410 can be an irrigation entry port configured to receive irrigation substance to flow into the irrigation channel 225. The distal connector end 418 can receive the irrigation substance from an external repository or container. The distal connector end 418 of the lavage connector 410 can connect to the pump device 240 to receive and push the irrigation substance through the irrigation channel 225. The pump device 240 connected to the lavage connector 410 can be a different pump device 240 than the one connected to the aspiration channel 222 and configured to suction the material 112.

Figure 5:
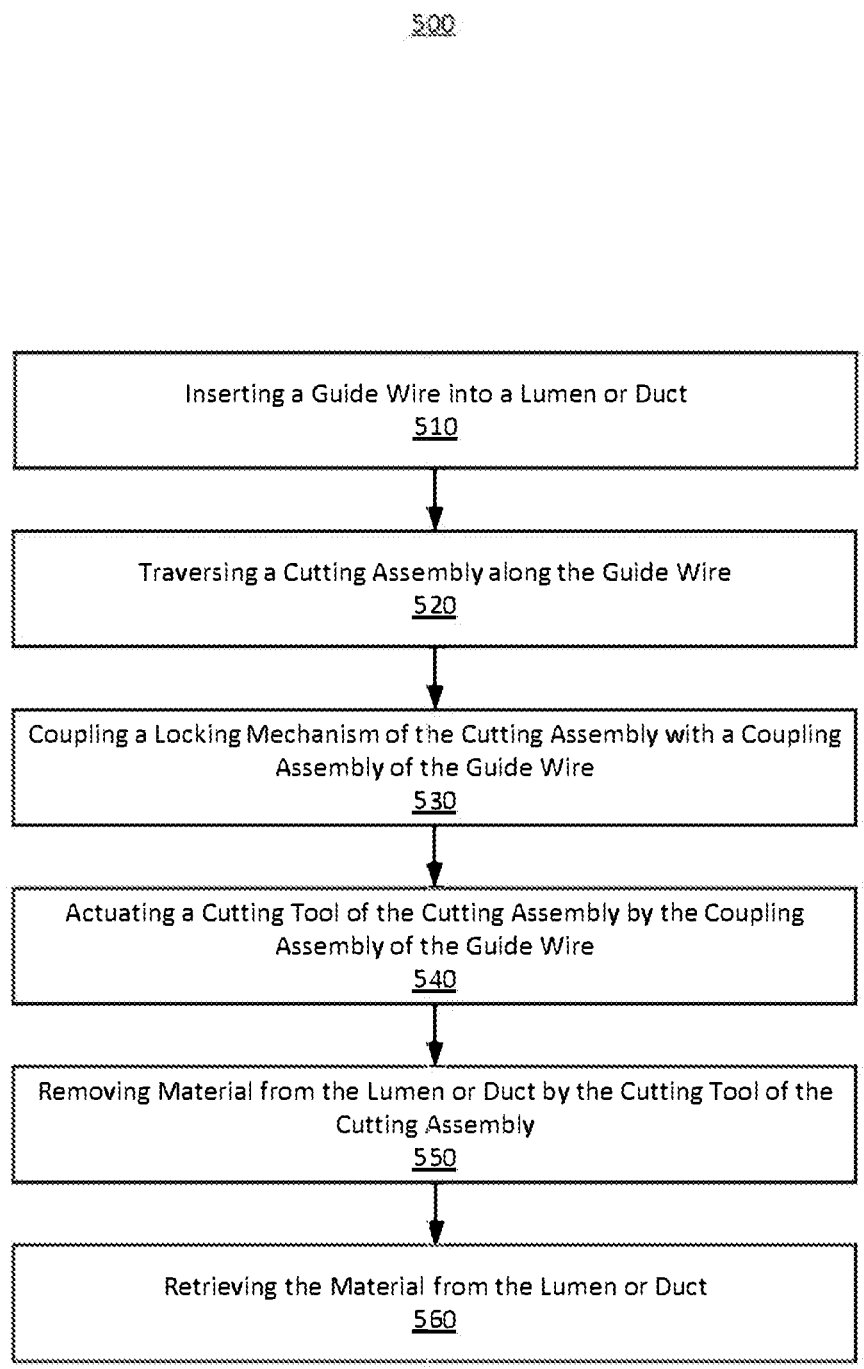
FIG. 5 is a flow diagram of a method of using the material removal system.

Referring to FIG. 5, shown is a method 500 of using the material removal system 115, the material removal system 200, the material removal system 300, or the material removal system 400 described herein. Various embodiments of the components described herein can perform the method 500. The method 500 or steps thereof can be repeated, such as to address multiple materials to be removed, both inside and outside the lumen or ducts.

At 510, a guide wire (e.g., guide wire 120) maneuvers into a lumen or duct (e.g., lumen or duct 110). In some embodiments, the operator can insert the guide wire as part of a surgical operation including one or more procedures for diagnosis and treatment, for example, by collecting at least one sample, removing at least one material (e.g., material 112), or widening narrow luminal tracts. The operator can introduce the cavity by identifying a bodily cavity, such as a sinus tract, lumen, or other natural hollow or sinus. The guide wire can maneuver into the lumen or duct via the cavity. The cavity can be a bodily cavity or a spacing inside the body, such as the mouth, the ear, the nose, the esophagus, pancreatic duct, or colon. At least one surgical procedure, such as percutaneous procedure, a cut, a drill, or a dissection can create the cavity. The created cavity can be in various different portions such as the arm, the stomach, the liver, the neck, or the kidney. In some embodiments, the guide wire maneuver as part of a percutaneous procedure that involves accessing organs or other tissue via a needle-puncture of the skin. The guidewire can also maneuver through a working channel of an endoscope. In one example, the guide wire maneuver from the proximal tube end of the cutting assembly to the distal tube end of the cutting assembly. The guide wire can maneuver through the hollow portion of the locking mechanism.

The guide wire can maneuver to the material within the lumen or duct. For example, the operator can determine a location of the material using non-intrusive imaging techniques, such as an x-ray, an ultrasound, magnetic resonance imaging ("MM"), or a computer tomography ("CT") scan. In some embodiments, the operator can push, drive, or otherwise navigate the guide wire into the lumen or duct. In some embodiments, a driving device such as robotically assisted force can push, drive, or otherwise navigate the guide wire into the lumen or duct. In some embodiments, other electrically powered devices can push, drive, or otherwise navigate the guide wire into the lumen or duct. In some embodiments, the guide wire maneuvers through the lumen or duct by bouncing, turning, or adjusting a navigation direction in response to at least a contact with the lumen or duct wall. The guide wire can include a compound that causes the guide wire to radiopaque while being navigated. The luminescence allows the operator to maneuver the guide wire using fluoroscopic imaging techniques. The attachments can facilitate identification of the material in the lumen or duct, such as to receive visual feedback to indicate the material in the lumen or duct. In some embodiments, navigating the guide wire in the lumen or duct and using the one or more sensors can identify the material. In some embodiments, the camera or the light source can identify the material. The operator can use a display device to see the data transmitted from the camera or the light source.

In some embodiments, the pump device provides the irrigation substance via the delivery channel of the guide wire for release at the distal wire end. The pump device can irrigate the cavity, lumen or duct, or the material as the guide wire navigates within the lumen or duct to the material.

The guide wire can reach the material. The guide wire can reach the material based on, for example, sensing a blockage within the lumen or duct using the one or more sensors. A display device connected to the guide wire can display an image of the material from the camera. In some embodiments, the navigation or driving of the guide wire terminates in response to reaching the material. In some embodiments, the navigation or driving of the guide wire terminates in response to being in contact with the material. In some embodiments, the navigation or driving of the guide wire terminates in response to passing the material. The guide wire can pass the material, such as through the material located in the lumen or duct. The distal wire end of the guide wire can position a distance from the material. The distance can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm from the material.

At 520, a cutting assembly (e.g., cutting assembly 130) maneuvers along the guide wire. In some embodiments, the cutting assembly maneuvers into the lumen or duct separately from the guide wire. For example, the cutting assembly maneuvers into the lumen or duct via the cavity subsequent to the insertion of the guide wire. The operator can insert the cutting assembly, enclosing the guide wire, into the lumen or duct. The operator can use at least one external device, such as the motor the display device, to assist with navigation of the cutting assembly. The cutting assembly can maneuver along the guide wire to proceed into the lumen or duct.

In some embodiments, the cutting assembly can retract or pull back the guide wire into or through the cutting assembly as the cutting assembly maneuver along the guide wire. While moving towards the material, the cutting assembly can push or exert a force to the proximal wire end. The guide wire can retract in response to the force exerted to the proximal wire end, as to terminate further extension of the distal wire end of the guide wire. In some embodiments, the cutting assembly can extend or retract the guide wire, for example, by a manual operation or the motor. The retracted guide wire can be stored, for example, in a guide wire storage located either internal to or external from the cutting assembly. The guide wire can retract to decrease the length between the proximal wire end and the distal wire end of the guide wire.

The cutting assembly can traverse through the lumen or duct. The cutting assembly can maneuver from the proximal wire end to enter the lumen or duct and traverse to the distal wire end to reach the material. The cutting assembly can introduce the irrigation substance to into the lumen or duct while traversing the guide wire. For example, at this point, the guide wire is in a location that is a distance away from the distal tube end of the cutting assembly within the lumen or duct. The cutting assembly can maneuver or pull itself towards the distal wire end of the guide wire. The cutting assembly can maneuver in the lumen or duct using the guide wire. For example, if the guide wire includes 40 degrees bend between a first location to a second location, the cutting assembly can maneuver from the first location, bend 40 degrees similar to the guide wire, and maneuver towards the second location. The first location can be a location at which the locking mechanism of the cutting assembly is adjacent to the proximal wire end. The second location can be a location at which the locking mechanism of the cutting assembly is adjacent to the material. In some embodiments, the cutting assembly can maneuver along the guide wire to a coupling assembly (e.g., coupling assembly 140) of the guide wire.

At 530, a locking mechanism (e.g., locking mechanism 150) of the cutting assembly couples with the coupling assembly of the guide wire. The cutting assembly can maneuver along the guide wire towards the coupling assembly. The cutting assembly couples with the guide wire by coupling the locking mechanism to the coupling assembly. The locking mechanism can couple with the coupling assembly using one or more engagement, locking, or coupling techniques, such as friction fit, pin interconnection, torque fit, rotating coupling, snap ring, or other coupling or fastening techniques to interlock or connect multiple components together. For example, if the locking mechanism includes a circular hollow portion, the coupling assembly can include a circular protruding portion that couples with the locking mechanism.

The locking mechanism can couple with the coupling assembly via a magnetic force. For example, the cutting assembly can reach the coupling assembly using the guide wire. The cutting assembly can be close or near to the coupling assembly, such as 1, 2, 3, 4, 5, 6, 7, 8, 9, or 10 cm from the coupling assembly. The magnetic force between the coupling assembly and the locking mechanism can attract or pull the locking mechanism of the cutting assembly to couple with the magnet of the coupling assembly. For example, the cutting assembly can maneuver towards the coupling assembly located on the guide wire. The cutting assembly can approach a certain distance within range of the magnetic or electromagnetic force. The locking mechanism can attract the coupling assembly (or vice versa). Subsequently, and as an example, the cutting assembly with the locking mechanism can pull towards the coupling assembly. The locking mechanism can couple with the coupling assembly, once the locking mechanism is in contact with the coupling assembly.

The locking mechanism can couple with the coupling assembly via an electromagnetic force. In some embodiments, the cutting assembly can introduce electrical power to the locking mechanism to couple the locking mechanism with the coupling assembly via electromagnetic force. In some embodiments, the motor applies a current to the guide wire such that the guide wire can couple with the locking mechanism via electromagnetic force. The current can also introduce electrical power to the cutting tool. The motor can continuously provide the electrical power. In some embodiments, the locking mechanism disengages from the coupling assembly by terminating the electrical power. The magnetic field terminates by blocking the electrical power to terminate the current flowing to the guide wire composed with the magnetic material. The termination of the electrical power can be to the coupling assembly or the locking mechanism. When the guide wire is demagnetized, the coupling assembly will de-couple from the locking mechanism of the cutting assembly.

At 540, the coupling assembly of the guide wire actuates a cutting tool (e.g., cutting tool 160) of the cutting assembly. The guide wire can rotate in response to receiving an exerted rotational force or torque at the proximal wire end. The motor coupled to the proximal wire end of the guide wire can provide the torque. In some embodiments, the operator can exert a manual or mechanism rotation to the guide wire. The motor can provide torque at the proximal wire end of the guide wire. The exerted rotation can traverse from the proximal wire end to the distal wire end of the guide wire. For example, the motor can provide torque to the proximal wire end of the guide wire. The torque can traverse from the proximal wire end to the distal wire end of the guide wire.

The guide wire can rotate the coupling assembly. The rotation of the coupling assembly can be in response receiving torque provided by the motor. The coupling assembly, coupled to the locking mechanism, can provide the rotation to the cutting tool for debriding or removing the material from the lumen or duct. As an example, the motor can provide 180 degrees rotation to the guide wire. The guide wire can traverse the rotational force from the proximal wire end to the distal wire end. The distal wire end, in this example, can receive the rotation of 180 degrees from the motor. Accordingly, the coupling assembly can rotate 180 degrees.

In some embodiments, the motor is a first motor, and the first motor can rotate a second motor of the coupling assembly configured to rotate in response to the guide wire receiving a signal provided by the first motor. The first motor can provide the signal to the coupling assembly via the guide wire. The signal can specify a rotation for turning the coupling assembly. The rotation can be 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, or 360 degrees. The second motor can subsequently rotate based on the rotation specified in the signal. In some embodiments, the rotation by the coupling assembly occurs concurrent to the guide wire receiving the torque provided by the first motor. The first motor can provide multiple rotations to the proximal wire end of the guide wire. The multiple rotations can traverse from the proximal wire end towards the distal wire end of the guide wire. The coupling assembly, located on the guide wire, can rotate concurrent to each of the multiple rotations provided by the first motor. For example, the first motor can provide a 30-degree rotation and a signal to rotate the coupling assembly an additional 30 degrees. In response to the provided torque by the first motor, the coupling assembly can rotate 30 degree based on the provided torque. In response to the signal, the second motor can then rotate the coupling assembly an additional 30 degrees.

At 550, the cutting tool of the cutting assembly removes the material from the lumen or duct. The operator can initiate the rotation of the cutting assembly in response to positioning the distal tube end of the cutting assembly at or near the material. In some embodiments, the operator actuates the hand piece to actuate the cutting assembly. In some embodiments, the operator can actuate the motor to initiate the cutting assembly. The positioning of the cutting assembly can refer to, for example, in contact with, 0.1 mm, 0.2 mm, 0.3 mm, 0.4 mm, 0.5 mm, 1 mm, 1.5 mm, 2.0 mm, 2.5 mm, 3.0 mm, 4.0 mm, or 5.0 mm from the material. The cutting assembly can remove the material in response to the rotation by the guide wire.

The cutting tool of the cutting assembly can cut material in the lumen or duct while the first motor provides torque to the guide wire. The cutting tool can rotate responsive to receiving the torque provided by the first motor to remove the material from the lumen or duct. The cutting assembly can proceed to maneuver through the lumen or duct to remove additional portions of the material. For example, the coupling assembly can indicate the location material, such that in response to coupling the locking mechanism with the coupling assembly, the first motor can provide torque to the proximal wire end of the guide wire. Subsequently, the cutting tool can rotate in response to the guide wire receiving the torque provided by the first motor. In some embodiments, the cutting tool cuts the material tangentially or from the side via a cutting window (e.g., cutting window 310). In some embodiments, the cutting assembly traverses the material, which can be located within the lumen or duct, to penetrate, cut, or debride the material. In some embodiments, the first motor can provide the rotation continuously after the locking mechanism couples with the coupling assembly. In some other embodiments, in addition to the locking mechanism coupling with the coupling assembly, the first motor can provide the rotation while the cutting assembly is moving, and terminate the rotation if the cutting assembly stopped moving.

The cutting assembly can introduce irrigation substance to into the lumen or duct while cutting the material. The operator control the volume of irrigation substance provided to the irrigation channel (e.g., irrigation channel 225) via the pump device. In some embodiments, the material removal system receives the irrigation substance via the lavage connector (e.g., lavage connector 410). The pump device can provide or transmit irrigation substance through the irrigation channel of the cutting assembly to facilitate the debriding or cutting process. The irrigation substance can include liquid, gas, or other chemical compound to soften or breakdown the material. The irrigation substance can facilitate the process of debriding the material into the debrided materials, for example, by exerting a gaseous substance to soften, disperse, or breakdown the material. Accordingly, the provision of the irrigation substance can assist the debriding process using the cutting assembly. In another example, the irrigation substance can assist in healing the lumen or duct, for example, by unblocking a stenosed or narrowed a duct or by providing a medication to the treatment area within the duct or lumen.

The cutting assembly can use at least one sensor attached to the cutting assembly to determine that the material has been debrided, such as using a pressure sensor, impedance sensor, camera, a tilt sensor, or an impact sensor. The debrided materials can be determined by an absent of a tilt, an impact, or a visual feedback of the material.

At 560, the material removal system can retrieve the debrided material from the lumen or duct. The material removal system can collect the material as it debrides the material. While debriding the material, the material removal system can retrieve or draw in the debrided materials into the aspiration channel (e.g., aspiration channel 222). The pump device can pull in or withdraw the debrided material for collection or storage. The debrided materials can be stored in a container or a repository external to the material removal system. The material removal system 115 can withdraw the debrided materials as the cutting assembly traverses through the lumen or duct, or as the cutting assembly debrides the material. The pump device can apply a vacuum pressure greater than or equal to 50 mmHg. The pump device can apply a vacuum pressure less than or equal to 750 mmHg to retrieve the debrided materials through the aspiration channel. The debrided materials can be stored in the repository after the material removal system cuts the material. The operator can remove the material removal system and the guide wire in response to retrieving the debrided materials from the lumen or duct.

Although the present disclosure discloses various embodiments of a material removal system, including but not limited to the guide wire that can be fed through the length of the material removal system and the cutting assembly that can be attached to the tip of the material removal system, the scope of the present disclosure is not intended to be limited to such embodiments or to material removal system in general. Rather, the scope of the present disclosure extends to any device that can debride and remove tissues and/or necrotic material from within lumen or duct using a single tool. As such, the scope of the present disclosure extends to improved material removal systems that can be built with some or all of the components described herein. For instance, an improved material removal system with an integrated cutting assembly and configured to be coupled to a coupling assembly is also disclosed herein. Furthermore, the material removal system can also include predefined conduits that extend along the length of the cutting assembly such that the cutting assembly need not define the aspiration channel or the irrigation channel. In other embodiments, the aspiration channel is also predefined but made such that the aspiration channel is cleaned and purified for use with multiple subjects. Similarly, the cutting tool or the cutting assembly can also be a part of the material removal system, but also capable of being cleaned and purified for use with multiple subjects.

Furthermore, it should be understood by those skilled in the art that any or all of the components that constitute the material removal system can be built into an existing material removal system or into a newly designed material removal system for use in debriding and removing materials from within the lumen or duct.

Having now described some illustrative embodiments, it is apparent that the foregoing is illustrative and not limiting, having been presented by way of example. In particular, although many of the examples presented herein involve specific combinations of method acts or system elements, those acts and those elements can combine in other ways to accomplish the same objectives. Acts, elements and features discussed in connection with one embodiment are not intended to be excluded from a similar role in other embodiments.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate embodiments consisting of the items listed thereafter exclusively. In one embodiment, the systems and methods described herein consist of one, each combination of more than one, or all of the described elements, acts, or components.

Any references to embodiments or elements or acts of the systems and methods herein referred to in the singular can also embrace embodiments including a plurality of these elements, and any references in plural to any embodiment or element or act herein can also embrace embodiments including only a single element. References in the singular or plural form are not intended to limit the presently disclosed systems or methods, their components, acts, or elements to single or plural configurations. References to any act or element being based on any information, act or element can include embodiments where the act or element is based at least in part on any information, act, or element.

Any embodiment disclosed herein can be combined with any other embodiment or embodiment, and references to "an embodiment," "some embodiments," "one embodiment" or the like are not necessarily mutually exclusive and are intended to indicate that a particular feature, structure, or characteristic described in connection with the embodiment can be included in at least one embodiment. Such terms as used herein are not necessarily all referring to the same embodiment. Any embodiment can combine with any other embodiment, inclusively or exclusively, in any manner consistent with the aspects and embodiments disclosed herein.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

Systems and methods described herein can be embodied in other specific forms without departing from the characteristics thereof. Further relative parallel, perpendicular, vertical or other positioning or orientation descriptions include variations within +/−10% or +/−10 degrees of pure vertical, parallel or perpendicular positioning. References to "approximately," "about" "substantially" or other terms of degree include variations of +/−10% from the given measurement, unit, or range unless explicitly indicated otherwise. Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

The term "coupled" and variations thereof includes the joining of two members directly or indirectly to one another. Such joining can be stationary (e.g., permanent or fixed) or moveable (e.g., removable or releasable). Such joining can be achieved with the two members coupled directly with or to each other, with the two members coupled with each other using a separate intervening member and any additional intermediate members coupled with one another, or with the two members coupled with each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling can be mechanical, electrical, or fluidic.

References to "or" can be construed as inclusive so that any terms described using "or" can indicate any of a single, more than one, and all of the described terms. A reference to "at least one of 'A' and 'B'" can include only 'A', only 'B', as well as both 'A' and 'B'. Such references used in conjunction with "comprising" or other open terminology can include additional items.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

References herein to the positions of elements (e.g., "top," "bottom," "above," "below") are merely used to describe the orientation of various elements in the FIGURES. It should be noted that the orientation of various elements can differ according to other exemplary embodiments, and that such variations are intended to be encompassed by the present disclosure.

The invention claimed is:

1. A system for removing material from a lumen or duct, comprising:
    a guide wire extending from a proximal wire end to a distal wire end; and
    a cutting assembly comprising:
        a flexible tube extending from a proximal tube end to a distal tube end of the cutting assembly configured to be delivered through a flexible endoscope or via percutaneous access port;
        a cutting tool coupled to the distal tube end of the flexible tube, the cutting tool configured to remove the material; and
        a locking mechanism configured to couple with a coupling assembly of the guide wire to receive torque provided by a motor coupled to the proximal wire end of the guide wire to rotate the cutting tool to remove the material.

2. The system of claim 1, wherein the cutting assembly is further configured to maneuver from a first position at which the locking mechanism is adjacent to the proximal wire end to a second position at which the locking mechanism is adjacent to the distal wire end;
    the locking mechanism configured to couple with the coupling assembly of the guide wire positioned at the second position adjacent to the distal wire end of the guide wire; and
    the cutting tool configured to remove the material in response to the locking mechanism coupled with the coupling assembly and receiving the torque provided by the motor.

3. The system of claim 2, wherein the coupling assembly is configured to receive the torque provided by the motor in response to the guide wire receiving the torque provided by the motor.

4. The system of claim 1, wherein the locking mechanism comprises a first hollow portion and a first protruding portion; and
    the guide wire comprises the coupling assembly comprising:
        a second hollow portion opposite the first protruding portion of the locking mechanism; and
        a second protruding portion opposite the first hollow portion of the locking mechanism, wherein the coupling assembly is configured to form a friction fit with the locking mechanism.

5. The system of claim 1, wherein the locking mechanism is composed of a first magnetic material; and
    the guide wire comprises the coupling assembly composed of a second magnetic material configured to couple with the locking mechanism via a magnetic coupling.

6. The system of claim 1, wherein the cutting assembly comprises one or more sensors configured to receive image data and detect the material within the lumen or duct.

7. The system of claim 6, wherein the guide wire comprises the one or more sensors configured to facilitate movement of the guide wire towards the material.

8. The system of claim 1, wherein the cutting tool comprises a fluoroscopic marker and at least one of a blade, a drill, a saw, a scoop, or a hook configured to remove the material.

9. They system of claim 1, wherein the locking mechanism is configured to couple with the guide wire when the cutting assembly is at a position at which the locking mechanism is adjacent to the material; and
    the cutting tool configured to remove the material in response to the locking mechanism coupling with the guide wire at the position adjacent to the material and the guide wire receiving the torque provided by the motor.

10. The system of claim 1, wherein the cutting assembly comprises:
    an aspiration channel configured to retrieve the material removed from the lumen or duct; and
    an irrigation channel configured to provide an irrigation substance to the lumen or duct, wherein the aspiration channel and the irrigation channel are connected to a pump device coupled to the proximal tube end of the cutting assembly.

11. The system of claim 1, wherein the locking mechanism of the cutting assembly comprises a hollow portion configured to route the guide wire to extend from the proximal tube end through the distal tube end; and the cutting assembly configured to maneuver from the proximal wire end of the guide wire towards the distal wire end of the guide wire, wherein the guide wire passes through the hollow portion of the locking mechanism.

12. The system of claim 1, wherein the guide wire extends out of the locking mechanism of the cutting assembly adjacent to the distal tube end of the cutting assembly, the guide wire configured to extend from the cutting assembly to maneuver within the lumen or duct.

13. The system of claim 1, wherein the guide wire comprises the coupling assembly configured to initiate a rotation in response to the guide wire receiving the torque provided by the motor; and the cutting tool configured to rotate in response to the rotation initiated by the motor.

14. A method for removing a material from a lumen or duct, comprising:

inserting a guide wire into the lumen or duct, the guide wire extending from a proximal wire end to a distal wire end;

moving a cutting assembly to the material using the guide wire, the cutting assembly comprising a flexible tube extending from a proximal tube end to a distal tube end, a cutting tool coupled to the distal tube end, and a locking mechanism;

coupling the locking mechanism of the cutting assembly with a coupling assembly of the guide wire;

removing, by the cutting tool in response to the guide wire receiving torque provided by a motor coupled to the proximal wire end, the material from the lumen or duct; and retrieving, through the cutting assembly, the material removed from the lumen or duct.

15. The method of claim 14, further comprising:

moving the cutting assembly from a first position at which the locking mechanism is adjacent to the proximal wire end to a second position at which the locking mechanism is adjacent to the material; and coupling the locking mechanism with the coupling assembly of the guide wire at the second position on the guide wire, the coupling assembly configured to rotate in response to the guide wire receiving the torque provided by the motor.

16. The method of claim 15, wherein the locking mechanism comprises a first hollow portion and a first protruding portion; and wherein the coupling assembly of the guide wire comprises:

a second hollow portion opposite the first protruding portion of the locking mechanism; and a second protruding portion opposite the first hollow portion of the locking mechanism, wherein the coupling assembly is configured to form a friction fit with the locking mechanism.

17. The method of claim 15, further comprising:

providing, by an external power source, an electric current through the guide wire to magnetize the coupling assembly composed of a first magnetic material;

engaging the magnetized coupling assembly to the locking mechanism composed of a second magnetic material;

terminating, by the external power source, the electric current through the guide wire to demagnetize the coupling assembly; and disengaging the demagnetized coupling assembly from the locking mechanism.

18. The method of claim 14, further comprising:

providing, through an irrigation channel of the cutting assembly, an irrigation substance into the lumen or duct; and retrieving, through an aspiration channel of the cutting assembly, the material removed from the lumen or duct in response to the cutting tool removing the material.

19. The method of claim 14, wherein the proximal wire end of the guide wire is fixed to the locking mechanism of the cutting assembly adjacent to the distal tube end of the cutting assembly, and further comprising:

extending the distal wire end of the guide wire from the proximal wire end;

moving the cutting assembly towards the distal wire end of the guide wire; and retracting the distal wire end of the guide wire to the proximal wire end in response to the cutting assembly moving towards the distal wire end.

20. The method of claim 14, wherein the motor is a first motor, and further comprising:

coupling the locking mechanism of the cutting assembly with the guide wire using the coupling assembly comprising a second motor;

initiating, by the second motor of the coupling assembly, a second rotation in response to the guide wire receiving the torque provided by the first motor; and removing, by the cutting tool, responsive to the second rotation, the material from the lumen or duct.

* * * * *